(12) United States Patent
Elimelech et al.

(10) Patent No.: US 11,801,115 B2
(45) Date of Patent: *Oct. 31, 2023

(54) MIRRORING IN IMAGE GUIDED SURGERY

(71) Applicant: AUGMEDICS LTD., Yokneam (IL)

(72) Inventors: Nissan Elimelech, Beerotaim (IL); Stuart Wolf, Yokneam (IL); Nitzan Krasney, Haifa (IL)

(73) Assignee: AUGMEDICS LTD., Yokneam Illit (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/827,710

(22) Filed: May 29, 2022

(65) Prior Publication Data
US 2022/0304768 A1  Sep. 29, 2022

Related U.S. Application Data

(63) Continuation of application No. 16/724,297, filed on Dec. 22, 2019, now Pat. No. 11,382,712.

(51) Int. Cl.
A61B 90/00 (2016.01)
G06T 11/00 (2006.01)
(Continued)

(52) U.S. Cl.
CPC ............ *A61B 90/37* (2016.02); *A61B 90/361* (2016.02); *G06T 7/73* (2017.01); *G06T 11/00* (2013.01);
(Continued)

(58) Field of Classification Search
CPC . A61B 90/37; A61B 90/361; A61B 2090/373; A61B 2090/372;
(Continued)

(56) References Cited

U.S. PATENT DOCUMENTS 3,101,715 A    8/1963  Glassman
3,690,776 A    9/1972  Zaporoshan
(Continued)

FOREIGN PATENT DOCUMENTS

CA    3022448 A1    2/2018
CA    3034314 A1    2/2018
(Continued)

OTHER PUBLICATIONS

US 11,395,705 B2, 09/2022, Lang (withdrawn)
(Continued)

*Primary Examiner* — Sing-Wai Wu
*Assistant Examiner* — Khoa Vu
(74) *Attorney, Agent, or Firm* — KNOBBE, MARTENS, OLSON & BEAR, LLP

(57) ABSTRACT

An imaging system, including a head-mounted display worn by a system operator. A marker defines a plane when attached to a human subject. Optically reflective elements are disposed on the marker and on opposing sides of the plane in a non-symmetrical arrangement with respect to the plane. A memory stores a graphical representation of a tool used in a procedure performed on the human subject, and an image of anatomy of the human subject. A camera attached to the display acquires an image of the marker and the tool. A processor analyzes the image to identify the plane and to identify a side of the plane wherein the camera is located, and to render to the display the image of the anatomy of the human subject with the graphical representation of the tool superimposed thereon from a point of view in the identified side of the plane.

20 Claims, 9 Drawing Sheets

(51) Int. Cl.
    *G06T 7/73* (2017.01)
    *A61B 90/50* (2016.01)
(52) U.S. Cl.
    CPC ... *A61B 2090/372* (2016.02); *A61B 2090/373* (2016.02); *A61B 2090/3937* (2016.02); *A61B 2090/502* (2016.02); *G06T 2207/30204* (2013.01)
(58) Field of Classification Search
    CPC ..... A61B 2090/502; G06T 7/73; G06T 11/00; G06T 2207/30204
    See application file for complete search history.

(56) References Cited

U.S. PATENT DOCUMENTS

| | | |
|---|---|---|
| 4,459,358 A | 7/1984 | Berke |
| 4,711,512 A | 12/1987 | Upatnieks |
| 4,863,238 A | 9/1989 | Brewster |
| 4,944,739 A | 7/1990 | Torre |
| 5,147,365 A | 9/1992 | Whitlock et al. |
| 5,441,042 A | 8/1995 | Putman |
| 5,442,146 A | 8/1995 | Bell |
| 5,510,832 A | 4/1996 | Garcia |
| D370,309 S | 5/1996 | Stucky |
| 5,665,092 A | 9/1997 | Mangiardi et al. |
| 5,771,121 A | 6/1998 | Hentschke |
| 5,792,046 A | 8/1998 | Dobrovolny |
| 5,841,507 A | 11/1998 | Barnes |
| 6,006,126 A | 12/1999 | Cosman |
| 6,038,467 A | 3/2000 | De Bliek et al. |
| 6,125,164 A | 9/2000 | Murphy |
| 6,147,805 A | 11/2000 | Fergason |
| 6,227,667 B1 | 5/2001 | Halldorsson |
| 6,256,529 B1 | 7/2001 | Holupka et al. |
| 6,285,505 B1 | 9/2001 | Melville et al. |
| 6,314,310 B1 | 11/2001 | Ben-Haim et al. |
| 6,349,001 B1 | 2/2002 | Spitzer |
| 6,444,192 B1 | 9/2002 | Mattrey |
| 6,449,090 B1 | 9/2002 | Omar |
| 6,456,405 B2 | 9/2002 | Horikoshi et al. |
| 6,456,868 B2 | 9/2002 | Saito et al. |
| 6,474,159 B1 | 11/2002 | Foxlin et al. |
| 6,518,939 B1 | 2/2003 | Kikuchi |
| 6,527,777 B2 | 3/2003 | Justin |
| 6,529,331 B2 | 3/2003 | Massof et al. |
| 6,549,645 B1 | 4/2003 | Oikawa |
| 6,578,962 B1 | 6/2003 | Amir et al. |
| 6,609,022 B2 | 8/2003 | Vilsmeier et al. |
| 6,610,009 B2 | 8/2003 | Person |
| D480,476 S | 10/2003 | Martinson et al. |
| 6,659,611 B2 | 12/2003 | Amir et al. |
| 6,675,040 B1 | 1/2004 | Cosman |
| 6,683,584 B2 | 1/2004 | Ronzani et al. |
| 6,690,964 B2 | 2/2004 | Bieger et al. |
| 6,714,810 B2 | 3/2004 | Grzeszczuk et al. |
| 6,737,425 B1 | 5/2004 | Yamamoto |
| 6,740,882 B2 | 5/2004 | Weinberg |
| 6,757,068 B2 | 6/2004 | Foxlin |
| 6,759,200 B1 | 7/2004 | Stanton |
| 6,847,336 B1 | 1/2005 | Emelson et al. |
| 6,856,324 B2 | 2/2005 | Sauer |
| 6,856,826 B2 | 2/2005 | Seeley et al. |
| 6,891,518 B2 | 5/2005 | Sauer et al. |
| 6,900,777 B1 | 5/2005 | Hebert et al. |
| 6,919,867 B2 | 7/2005 | Sauer |
| 6,921,167 B2 | 7/2005 | Nagata |
| 6,966,668 B2 | 11/2005 | Cugini |
| 6,980,849 B2 | 12/2005 | Sasso |
| 6,993,374 B2 | 1/2006 | Sasso |
| 6,997,552 B1 | 2/2006 | Hung |
| 6,999,239 B1 | 2/2006 | Martins et al. |
| 7,035,371 B2 | 4/2006 | Boese et al. |
| 7,043,961 B2 | 5/2006 | Pandey et al. |
| 7,103,233 B2 | 9/2006 | Stearns |
| 7,107,091 B2 | 9/2006 | Jutras et al. |
| 7,112,656 B2 | 9/2006 | Desnoyers |
| 7,141,812 B2 | 11/2006 | Appleby |
| 7,157,459 B2 | 1/2007 | Ohta |
| 7,169,785 B2 | 1/2007 | Timmer |
| 7,171,255 B2 | 1/2007 | Holupka et al. |
| 7,176,936 B2 | 2/2007 | Sauer et al. |
| 7,187,792 B2 | 3/2007 | Fu |
| 7,190,331 B2 | 3/2007 | Genc et al. |
| 7,194,295 B2 | 3/2007 | Vilsmeier |
| 7,215,322 B2 | 5/2007 | Genc et al. |
| 7,229,078 B2 | 6/2007 | Echot |
| 7,231,076 B2 | 6/2007 | Fu |
| 7,235,076 B2 | 6/2007 | Pacheco |
| 7,239,330 B2 | 7/2007 | Sauer et al. |
| 7,241,292 B2 | 7/2007 | Hooven |
| 7,259,266 B2 | 8/2007 | Carter |
| 7,260,426 B2 | 8/2007 | Schweikard |
| 7,269,192 B2 | 9/2007 | Hayashi |
| 7,281,826 B2 | 10/2007 | Huang |
| 7,320,556 B2 | 1/2008 | Vagn-Erik |
| 7,330,578 B2 | 2/2008 | Wang |
| 7,359,535 B2 | 4/2008 | Salla |
| 7,364,314 B2 | 4/2008 | Nilsen et al. |
| 7,366,934 B1 | 4/2008 | Narayan et al. |
| 7,379,077 B2 | 5/2008 | Bani-Hashemi |
| 7,431,453 B2 | 10/2008 | Hogan |
| 7,435,219 B2 | 10/2008 | Kim |
| 7,458,977 B2 | 12/2008 | McGinley |
| 7,462,852 B2 | 12/2008 | Appleby |
| 7,493,153 B2 | 2/2009 | Ahmed et al. |
| 7,505,617 B2 | 3/2009 | Fu |
| 7,507,968 B2 | 3/2009 | Wollenweber |
| 7,518,136 B2 | 4/2009 | Appleby |
| 7,525,735 B2 | 4/2009 | Sottilare et al. |
| D592,691 S | 5/2009 | Chang |
| D592,692 S | 5/2009 | Chang |
| D592,693 S | 5/2009 | Chang |
| 7,536,216 B2 | 5/2009 | Geiger et al. |
| 7,542,791 B2 | 6/2009 | Mire |
| 7,556,428 B2 | 7/2009 | Sukovic et al. |
| 7,557,824 B2 | 7/2009 | Holliman |
| 7,563,228 B2 | 7/2009 | Ma et al. |
| 7,567,834 B2 | 7/2009 | Clayton |
| 7,586,686 B1 | 9/2009 | Hall |
| D602,620 S | 10/2009 | Cristoforo |
| 7,605,826 B2 | 10/2009 | Sauer |
| 7,606,613 B2 | 10/2009 | Simon et al. |
| 7,607,775 B2 | 10/2009 | Hermanson |
| 7,620,223 B2 | 11/2009 | Xu |
| 7,627,085 B2 | 12/2009 | Boyden et al. |
| 7,630,753 B2 | 12/2009 | Simon et al. |
| 7,633,501 B2 | 12/2009 | Wood |
| 7,645,050 B2 | 1/2010 | Wilt |
| 7,653,226 B2 | 1/2010 | Guhring et al. |
| 7,689,019 B2 | 3/2010 | Boese |
| 7,689,042 B2 | 3/2010 | Brunner |
| 7,689,320 B2 | 3/2010 | Prisco |
| 7,699,486 B1 | 4/2010 | Beiner |
| 7,699,793 B2 | 4/2010 | Gotte |
| 7,719,769 B2 | 5/2010 | Sugihara et al. |
| D617,825 S | 6/2010 | Chang |
| D619,285 S | 7/2010 | Cristoforo |
| 7,751,865 B2 | 7/2010 | Jascob et al. |
| 7,758,204 B2 | 7/2010 | Klipstein |
| 7,768,702 B2 | 8/2010 | Hirose et al. |
| 7,769,236 B2 | 8/2010 | Fiala |
| 7,773,074 B2 | 8/2010 | Arenson et al. |
| 7,774,044 B2 | 8/2010 | Sauer et al. |
| 7,822,483 B2 | 10/2010 | Stone et al. |
| D628,307 S | 11/2010 | Krause-Bonte |
| 7,826,902 B2 | 11/2010 | Stone et al. |
| 7,831,096 B2 | 11/2010 | Williamson |
| 7,835,778 B2 | 11/2010 | Foley |
| 7,835,784 B2 | 11/2010 | Mire |
| 7,837,987 B2 | 11/2010 | Shi |
| 7,840,093 B2 | 11/2010 | Fu et al. |
| 7,840,253 B2 | 11/2010 | Tremblay et al. |
| 7,840,256 B2 | 11/2010 | Akin et al. |

(56) References Cited

U.S. PATENT DOCUMENTS

| | | |
|---|---|---|
| 7,853,305 B2 | 12/2010 | Simon |
| 7,854,705 B2 | 12/2010 | Pawluczyk |
| 7,857,271 B2 | 12/2010 | Lees |
| 7,860,282 B2 | 12/2010 | Boese |
| D630,766 S | 1/2011 | Harbin |
| 7,865,269 B2 | 1/2011 | Prisco |
| 7,874,686 B2 | 1/2011 | Rossner et al. |
| 7,881,770 B2 | 2/2011 | Melkent et al. |
| 7,893,413 B1 | 2/2011 | Appleby |
| 7,894,649 B2 | 2/2011 | Fu |
| 7,920,162 B2 | 4/2011 | Masini et al. |
| 7,938,553 B1 | 5/2011 | Beiner |
| 7,945,310 B2 | 5/2011 | Gattani |
| 7,953,471 B2 | 5/2011 | Clayton |
| 7,969,383 B2 | 6/2011 | Eberl et al. |
| 7,974,677 B2 | 7/2011 | Mire |
| 7,985,756 B2 | 7/2011 | Barlow |
| 7,991,557 B2 | 8/2011 | Liew |
| 7,993,353 B2 | 8/2011 | Robner et al. |
| 7,996,064 B2 | 8/2011 | Simon et al. |
| 8,004,524 B2 | 8/2011 | Deinzer |
| 8,021,300 B2 | 9/2011 | Ma et al. |
| 8,022,984 B2 | 9/2011 | Cheong |
| 8,045,266 B2 | 10/2011 | Nakamura |
| 8,060,181 B2 | 11/2011 | Ponce |
| 8,068,581 B2 | 11/2011 | Boese et al. |
| 8,068,896 B2 | 11/2011 | Daghighian |
| 8,077,943 B2 | 12/2011 | Wiliams |
| 8,079,957 B2 | 12/2011 | Ma et al. |
| 8,085,075 B2 | 12/2011 | Huffman |
| 8,085,897 B2 | 12/2011 | Morton |
| 8,090,175 B2 | 1/2012 | Fu |
| 8,092,400 B2 | 1/2012 | Warkentine |
| 8,108,072 B2 | 1/2012 | Zhao |
| 8,112,292 B2 | 2/2012 | Simon |
| 8,116,847 B2 | 2/2012 | Gattani et al. |
| 8,120,847 B2 | 2/2012 | Chang |
| 8,121,255 B2 | 2/2012 | Sugiyama |
| 8,155,479 B2 | 4/2012 | Hoffman |
| 8,180,429 B2 | 5/2012 | Sasso |
| 8,208,599 B2 | 6/2012 | Ye |
| 8,221,402 B2 | 7/2012 | Francischelli |
| 8,239,001 B2 | 8/2012 | Verard et al. |
| 8,244,012 B2 | 8/2012 | Liang et al. |
| 8,253,778 B2 | 8/2012 | Atsushi |
| 8,271,069 B2 | 9/2012 | Jascob et al. |
| 8,280,491 B2 | 10/2012 | Kuduvalli et al. |
| 8,285,021 B2 | 10/2012 | Boese |
| 8,300,315 B2 | 10/2012 | Kobayashi |
| 8,305,685 B2 | 11/2012 | Heine |
| 8,306,305 B2 | 11/2012 | Porat et al. |
| 8,309,932 B2 | 11/2012 | Haselman |
| 8,317,320 B2 | 11/2012 | Huang |
| 8,328,815 B2 | 12/2012 | Farr et al. |
| 8,335,553 B2 | 12/2012 | Rubner |
| 8,335,557 B2 | 12/2012 | Maschke |
| 8,340,379 B2 | 12/2012 | Razzaque et al. |
| 8,369,925 B2 | 2/2013 | Giesel |
| 8,386,022 B2 | 2/2013 | Jutras et al. |
| 8,394,144 B2 | 3/2013 | Zehavi |
| 8,398,541 B2 | 3/2013 | DiMaio et al. |
| 8,444,266 B2 | 5/2013 | Waters |
| 8,457,719 B2 | 6/2013 | Moctezuma De La Barrera et al. |
| 8,467,851 B2 | 6/2013 | Mire et al. |
| 8,469,902 B2 | 6/2013 | Dick |
| 8,494,612 B2 | 7/2013 | Vetter et al. |
| 8,509,503 B2 | 8/2013 | Nahum et al. |
| 8,511,827 B2 | 8/2013 | Hua et al. |
| 8,531,394 B2 | 9/2013 | Maltz |
| 8,540,364 B2 | 9/2013 | Waters |
| 8,545,012 B2 | 10/2013 | Waters |
| 8,548,567 B2 | 10/2013 | Maschke et al. |
| 8,556,883 B2 | 10/2013 | Saleh |
| 8,559,596 B2 | 10/2013 | Thomson |
| 8,567,945 B2 | 10/2013 | Waters |
| 8,571,353 B2 | 10/2013 | Watanabe |
| 8,585,598 B2 | 11/2013 | Razzaque et al. |
| 8,600,001 B2 | 12/2013 | Schweizer |
| 8,600,477 B2 | 12/2013 | Beyar |
| 8,605,199 B2 | 12/2013 | Francisco |
| 8,611,988 B2 | 12/2013 | Miyamoto |
| 8,612,024 B2 | 12/2013 | Stone et al. |
| 8,634,897 B2 | 1/2014 | Simon |
| 8,641,621 B2 | 2/2014 | Razzaque et al. |
| 8,643,950 B2 | 2/2014 | König |
| 8,644,907 B2 | 2/2014 | Hartmann et al. |
| 8,674,902 B2 | 3/2014 | Park |
| 8,686,923 B2 | 4/2014 | Eberl et al. |
| 8,690,581 B2 | 4/2014 | Ruf et al. |
| 8,690,776 B2 | 4/2014 | Razzaque et al. |
| 8,692,845 B2 | 4/2014 | Fedorovskaya et al. |
| 8,693,632 B2 | 4/2014 | Allison |
| 8,694,075 B2 | 4/2014 | Groszmann |
| 8,699,765 B2 | 4/2014 | Hao |
| 8,705,829 B2 | 4/2014 | Frank |
| 8,737,708 B2 | 5/2014 | Hartmann et al. |
| 8,746,887 B2 | 6/2014 | Shestak |
| 8,784,450 B2 | 7/2014 | Moskowitz et al. |
| 8,786,689 B1 | 7/2014 | Liu |
| D710,545 S | 8/2014 | Wu |
| D710,546 S | 8/2014 | Wu |
| 8,827,934 B2 | 9/2014 | Chopra et al. |
| 8,831,706 B2 | 9/2014 | Fu |
| 8,836,768 B1 | 9/2014 | Rafii et al. |
| 8,838,199 B2 | 9/2014 | Simon et al. |
| 8,848,977 B2 | 9/2014 | Bammer et al. |
| 8,855,395 B2 | 10/2014 | Baturin |
| 8,878,900 B2 | 11/2014 | Yang et al. |
| 8,885,177 B2 | 11/2014 | Ben-Yishai et al. |
| 8,890,772 B2 | 11/2014 | Woo |
| 8,890,773 B1 | 11/2014 | Pederson |
| 8,890,943 B2 | 11/2014 | Lee |
| 8,897,514 B2 | 11/2014 | Feikas |
| 8,900,131 B2 | 12/2014 | Chopra et al. |
| 8,903,150 B2 | 12/2014 | Star-Lack |
| 8,908,952 B2 | 12/2014 | Isaacs et al. |
| 8,911,358 B2 | 12/2014 | Koninckx et al. |
| 8,917,268 B2 | 12/2014 | Johnsen |
| 8,920,776 B2 | 12/2014 | Gaiger |
| 8,922,589 B2 | 12/2014 | Herzel |
| 8,941,559 B2 | 1/2015 | Bar-Zeev et al. |
| 8,942,455 B2 | 1/2015 | Chou |
| 8,950,877 B2 | 2/2015 | Northley et al. |
| 8,953,246 B2 | 2/2015 | Koenig |
| 8,965,583 B2 | 2/2015 | Ortmaier et al. |
| 8,969,829 B2 | 3/2015 | Wollenweber |
| 8,989,349 B2 | 3/2015 | Thomson |
| 8,992,580 B2 | 3/2015 | Bar |
| 8,994,729 B2 | 3/2015 | Nakamura |
| 8,994,795 B2 | 3/2015 | Oh |
| 9,004,711 B2 | 4/2015 | Gerolemou |
| 9,005,211 B2 | 4/2015 | Brundobler et al. |
| 9,011,441 B2 | 4/2015 | Bertagnoli et al. |
| 9,057,759 B2 | 6/2015 | Klingenbeck |
| 9,060,757 B2 | 6/2015 | Awson et al. |
| 9,066,751 B2 | 6/2015 | Sasso |
| 9,081,436 B1 | 7/2015 | Berme |
| 9,084,635 B2 | 7/2015 | Nuckley et al. |
| 9,085,643 B2 | 7/2015 | Svanborg |
| 9,087,471 B2 | 7/2015 | Miao |
| 9,100,643 B2 | 8/2015 | McDowall |
| 9,101,394 B2 | 8/2015 | Arata et al. |
| 9,111,175 B2 | 8/2015 | Strommer |
| 9,123,155 B2 | 9/2015 | Cunningham et al. |
| 9,125,556 B2 | 9/2015 | Zehavi |
| 9,129,054 B2 | 9/2015 | Nawana et al. |
| 9,129,372 B2 | 9/2015 | Kriston |
| 9,132,361 B2 | 9/2015 | Smithwick |
| 9,141,873 B2 | 9/2015 | Takemoto |
| 9,142,020 B2 | 9/2015 | Deguise et al. |
| 9,149,317 B2 | 10/2015 | Arthur et al. |
| 9,165,203 B2 | 10/2015 | McCarthy |
| 9,179,984 B2 | 11/2015 | Teichman et al. |
| D746,354 S | 12/2015 | Chang |

(56) References Cited

U.S. PATENT DOCUMENTS

| | | |
|---|---|---|
| 9,208,916 B2 | 12/2015 | Appleby |
| 9,220,573 B2 | 12/2015 | Kendrick et al. |
| 9,225,895 B2 | 12/2015 | Kozinski |
| 9,232,982 B2 | 1/2016 | Soler et al. |
| 9,235,934 B2 | 1/2016 | Mandella |
| 9,244,278 B2 | 1/2016 | Sugiyama et al. |
| 9,247,240 B2 | 1/2016 | Park |
| 9,259,192 B2 | 2/2016 | Ishihara |
| 9,265,572 B2 | 2/2016 | Fuchs et al. |
| 9,269,192 B2 | 2/2016 | Kobayashi |
| 9,283,052 B2 | 3/2016 | Ponce |
| 9,286,730 B2 | 3/2016 | Bar-Zeev et al. |
| 9,289,267 B2 | 3/2016 | Sauer et al. |
| 9,294,222 B2 | 3/2016 | Proctor, Jr. |
| 9,300,949 B2 | 3/2016 | Ahearn |
| 9,310,591 B2 | 4/2016 | Hua et al. |
| 9,320,474 B2 | 4/2016 | Demri |
| 9,323,055 B2 | 4/2016 | Baillot |
| 9,330,477 B2 | 5/2016 | Rappel |
| 9,335,547 B2 | 5/2016 | Takano et al. |
| 9,335,567 B2 | 5/2016 | Nakamura |
| 9,341,704 B2 | 5/2016 | Picard |
| 9,344,686 B2 | 5/2016 | Moharir |
| 9,349,066 B2 | 5/2016 | Koo |
| 9,349,520 B2 | 5/2016 | Demetriou |
| 9,364,294 B2 | 6/2016 | Razzaque et al. |
| 9,370,332 B2 | 6/2016 | Paladini et al. |
| 9,373,166 B2 | 6/2016 | Azar |
| 9,375,639 B2 | 6/2016 | Kobayashi et al. |
| 9,378,558 B2 | 6/2016 | Kajiwara et al. |
| 9,380,287 B2 | 6/2016 | Nistico |
| 9,387,008 B2 | 7/2016 | Sarvestani |
| 9,392,129 B2 | 7/2016 | Simmons |
| 9,395,542 B2 | 7/2016 | Tilleman et al. |
| 9,398,936 B2 | 7/2016 | Razzaque et al. |
| 9,400,384 B2 | 7/2016 | Griffith |
| 9,414,041 B2 | 8/2016 | Ko |
| 9,424,611 B2 | 8/2016 | Kanjirathinkal et al. |
| 9,424,641 B2 | 8/2016 | Wiemker |
| 9,438,894 B2 | 9/2016 | Park |
| 9,443,488 B2 | 9/2016 | Borenstein |
| 9,453,804 B2 | 9/2016 | Tahtali |
| 9,456,878 B2 | 10/2016 | Macfarlane et al. |
| 9,465,235 B2 | 10/2016 | Chang |
| 9,468,373 B2 | 10/2016 | Larsen |
| 9,470,908 B1 | 10/2016 | Frankel |
| 9,473,766 B2 | 10/2016 | Douglas |
| 9,492,222 B2 | 11/2016 | Singh |
| 9,495,585 B2 | 11/2016 | Bicer et al. |
| 9,498,132 B2 | 11/2016 | Maier-Hein et al. |
| 9,498,231 B2 | 11/2016 | Haider et al. |
| 9,507,155 B2 | 11/2016 | Morimoto |
| 9,513,495 B2 | 12/2016 | Waters |
| 9,521,966 B2 | 12/2016 | Schwartz |
| 9,526,443 B1 | 12/2016 | Berme |
| 9,530,382 B2 | 12/2016 | Simmons |
| 9,532,846 B2 | 1/2017 | Nakamura |
| 9,532,849 B2 | 1/2017 | Anderson et al. |
| 9,538,962 B1 | 1/2017 | Hannaford et al. |
| 9,545,233 B2 | 1/2017 | Sirpad |
| 9,546,779 B2 | 1/2017 | Rementer |
| 9,547,174 B2 | 1/2017 | Gao et al. |
| 9,547,940 B1 | 1/2017 | Sun et al. |
| 9,557,566 B2 | 1/2017 | Fujimaki |
| 9,560,318 B2 | 1/2017 | Reina et al. |
| 9,561,095 B1 | 2/2017 | Nguyen |
| 9,561,446 B2 | 2/2017 | Brecher |
| 9,565,415 B2 | 2/2017 | Zhang et al. |
| 9,572,661 B2 | 2/2017 | Robin |
| 9,576,556 B2 | 2/2017 | Simmons |
| 9,581,822 B2 | 2/2017 | Morimoto |
| 9,612,657 B2 | 4/2017 | Bertram et al. |
| 9,629,595 B2 | 4/2017 | Walker |
| 9,633,431 B2 | 4/2017 | Merlet |
| 9,645,395 B2 | 5/2017 | Bolas et al. |
| 9,646,423 B1 | 5/2017 | Sun et al. |
| 9,672,597 B2 | 6/2017 | Amiot |
| 9,672,640 B2 | 6/2017 | Kleiner |
| 9,675,306 B2 | 6/2017 | Morton |
| 9,675,319 B1 | 6/2017 | Razzaque |
| RE46,463 E | 7/2017 | Feinbloom |
| 9,710,968 B2 | 7/2017 | Dillavou et al. |
| 9,713,502 B2 | 7/2017 | Finkman |
| 9,724,119 B2 | 8/2017 | Hissong |
| 9,724,165 B2 | 8/2017 | Arata et al. |
| 9,726,888 B2 | 8/2017 | Giartisio |
| 9,728,006 B2 | 8/2017 | Varga |
| 9,729,831 B2 | 8/2017 | Birnkrant |
| 9,757,034 B2 | 9/2017 | Desjardins |
| 9,757,087 B2 | 9/2017 | Simon |
| 9,766,441 B2 | 9/2017 | Rappel |
| 9,767,608 B2 | 9/2017 | Lee et al. |
| 9,770,203 B1 | 9/2017 | Berme |
| 9,772,102 B1 | 9/2017 | Ferguson |
| 9,772,495 B2 | 9/2017 | Tam |
| 9,791,138 B1 | 10/2017 | Feinbloom |
| 9,800,995 B2 | 10/2017 | Libin |
| 9,805,504 B2 | 10/2017 | Zhang |
| 9,808,148 B2 | 11/2017 | Miller |
| 9,839,448 B2 | 12/2017 | Reckling et al. |
| 9,844,413 B2 | 12/2017 | Daon et al. |
| 9,851,080 B2 | 12/2017 | Wilt |
| 9,861,446 B2 | 1/2018 | Lang |
| 9,864,214 B2 | 1/2018 | Fass |
| 9,872,733 B2 | 1/2018 | Shoham et al. |
| 9,877,642 B2 | 1/2018 | Duret |
| 9,885,465 B2 | 2/2018 | Nguyen |
| 9,886,552 B2 | 2/2018 | Dillavou et al. |
| 9,892,564 B1 | 2/2018 | Cvetko et al. |
| 9,898,866 B2 | 2/2018 | Fuchs et al. |
| 9,901,414 B2 | 2/2018 | Lively |
| 9,911,187 B2 | 3/2018 | Steinle |
| 9,927,611 B2 | 3/2018 | Rudy |
| 9,928,629 B2 | 3/2018 | Benishti et al. |
| 9,940,750 B2 | 4/2018 | Dillavou et al. |
| 9,943,374 B2 | 4/2018 | Merritt et al. |
| 9,947,110 B2 | 4/2018 | Haimerl |
| 9,956,054 B2 | 5/2018 | Aguirre-Valencia |
| 9,958,674 B2 | 5/2018 | Border |
| 9,959,629 B2 | 5/2018 | Dillavou et al. |
| 9,965,681 B2 | 5/2018 | Border et al. |
| 9,968,297 B2 | 5/2018 | Connor |
| 9,980,780 B2 | 5/2018 | Lang |
| 9,986,228 B2 | 5/2018 | Woods |
| D824,523 S | 7/2018 | Paoli et al. |
| 10,010,379 B1 | 7/2018 | Gibby et al. |
| 10,013,531 B2 | 7/2018 | Richards |
| 10,015,243 B2 | 7/2018 | Kazerani et al. |
| 10,016,243 B2 | 7/2018 | Esterberg |
| 10,022,064 B2 | 7/2018 | Kim et al. |
| 10,022,065 B2 | 7/2018 | Yishai et al. |
| 10,022,104 B2 | 7/2018 | Sell et al. |
| 10,023,615 B2 | 7/2018 | Bonny |
| 10,026,015 B2 | 7/2018 | Cavusoglu |
| 10,034,713 B2 | 7/2018 | Yang et al. |
| 10,046,165 B2 | 8/2018 | Frewin |
| 10,066,816 B2 | 9/2018 | Chang |
| 10,073,515 B2 | 9/2018 | Awdeh |
| 10,080,616 B2 | 9/2018 | Wilkinson et al. |
| 10,082,680 B2 | 9/2018 | Chang |
| 10,085,709 B2 | 10/2018 | Lavallee et al. |
| 10,105,187 B2 | 10/2018 | Corndorf et al. |
| 10,107,483 B2 | 10/2018 | Oren |
| 10,108,833 B2 | 10/2018 | Hong et al. |
| 10,123,840 B2 | 11/2018 | Dorman |
| 10,130,378 B2 | 11/2018 | Bryan |
| 10,132,483 B1 | 11/2018 | Feinbloom |
| 10,134,166 B2 | 11/2018 | Benishti et al. |
| 10,134,194 B2 | 11/2018 | Kepner |
| 10,139,652 B2 | 11/2018 | Windham |
| 10,139,920 B2 | 11/2018 | Isaacs |
| 10,142,496 B1 | 11/2018 | Rao |
| 10,151,928 B2 | 12/2018 | Ushakov |
| 10,154,239 B2 | 12/2018 | Casas |

(56) References Cited

U.S. PATENT DOCUMENTS

| | | |
|---|---|---|
| 10,159,530 B2 | 12/2018 | Lang |
| 10,166,079 B2 | 1/2019 | McLachlin et al. |
| 10,175,507 B2 | 1/2019 | Nakamura |
| 10,175,753 B2 | 1/2019 | Boesen |
| 10,181,361 B2 | 1/2019 | Dillavou et al. |
| 10,186,055 B2 | 1/2019 | Takahashi |
| 10,188,672 B2 | 1/2019 | Wagner |
| 10,194,131 B2 | 1/2019 | Casas |
| 10,194,990 B2 | 2/2019 | Amanatullah et al. |
| 10,194,993 B2 | 2/2019 | Roger et al. |
| 10,195,076 B2 | 2/2019 | Fateh |
| 10,197,803 B2 | 2/2019 | Badiali et al. |
| 10,197,816 B2 | 2/2019 | Waisman |
| 10,207,315 B2 | 2/2019 | Appleby |
| 10,230,719 B2 | 3/2019 | Vaugn |
| 10,231,893 B2 | 3/2019 | Lei |
| 10,235,606 B2 | 3/2019 | Miao |
| 10,240,769 B1 | 3/2019 | Braganca |
| 10,247,965 B2 | 4/2019 | Ton |
| 10,251,724 B2 | 4/2019 | McLachlin et al. |
| 10,274,731 B2 | 4/2019 | Maimone |
| 10,278,777 B1 | 5/2019 | Lang |
| 10,292,768 B2 | 5/2019 | Lang |
| 10,296,805 B2 | 5/2019 | Yang et al. |
| 10,319,154 B1 | 6/2019 | Chakravarthula et al. |
| 10,326,975 B2 | 6/2019 | Casas |
| 10,339,719 B2 | 7/2019 | Jagga et al. |
| 10,352,543 B1 | 7/2019 | Braganca |
| 10,357,146 B2 | 7/2019 | Fiebel |
| 10,357,574 B2 | 7/2019 | Hilderbrand |
| 10,366,489 B2 | 7/2019 | Boettger et al. |
| 10,368,947 B2 | 8/2019 | Lang |
| 10,368,948 B2 | 8/2019 | Tripathi |
| 10,382,748 B2 | 8/2019 | Benishti et al. |
| 10,383,654 B2 | 8/2019 | Yilmaz et al. |
| 10,386,645 B2 | 8/2019 | Shousha |
| 10,398,514 B2 | 9/2019 | Ryan et al. |
| 10,405,927 B1 | 9/2019 | Lang |
| 10,419,655 B2 | 9/2019 | Sivan |
| 10,420,626 B2 | 9/2019 | Tokuda et al. |
| 10,420,813 B2 | 9/2019 | Newell-Rogers |
| 10,424,115 B2 | 9/2019 | Ellerbrock |
| 10,426,554 B2 | 10/2019 | Siewerdsen et al. |
| 10,431,008 B2 | 10/2019 | Djajadiningrat |
| 10,433,814 B2 | 10/2019 | Razzaque |
| 10,434,335 B2 | 10/2019 | Takahashi |
| 10,444,514 B2 | 10/2019 | Abou Shousha et al. |
| 10,447,947 B2 | 10/2019 | Liu |
| 10,448,003 B2 | 10/2019 | Grafenberg |
| 10,449,040 B2 | 10/2019 | Lashinski |
| 10,453,187 B2 | 10/2019 | Peterson |
| 10,463,434 B2 | 11/2019 | Siegler et al. |
| 10,465,892 B1 | 11/2019 | Feinbloom |
| 10,470,732 B2 | 11/2019 | Baumgart |
| 10,473,314 B1 | 11/2019 | Braganca |
| 10,485,989 B2 | 11/2019 | Jordan |
| 10,488,663 B2 | 11/2019 | Choi |
| D869,772 S | 12/2019 | Gand |
| D870,977 S | 12/2019 | Berggren et al. |
| 10,499,997 B2 | 12/2019 | Weinstein et al. |
| 10,504,231 B2 | 12/2019 | Fiala |
| 10,507,066 B2 | 12/2019 | DiMaio |
| 10,511,822 B2 | 12/2019 | Casas |
| 10,517,544 B2 | 12/2019 | Taguchi |
| 10,537,395 B2 | 1/2020 | Perez |
| 10,540,780 B1 | 1/2020 | Cousins |
| 10,543,485 B2 | 1/2020 | Ismagilov |
| 10,546,423 B2 | 1/2020 | Jones et al. |
| 10,548,557 B2 | 2/2020 | Lim |
| 10,555,775 B2 | 2/2020 | Hoffman |
| 10,568,535 B2 | 2/2020 | Roberts et al. |
| 10,571,696 B2 | 2/2020 | Urey et al. |
| 10,571,716 B2 | 2/2020 | Chapiro |
| 10,573,087 B2 | 2/2020 | Gallop |
| 10,602,114 B2 | 2/2020 | Casas |
| 10,577,630 B2 | 3/2020 | Zhang |
| 10,586,400 B2 | 3/2020 | Douglas |
| 10,592,748 B1 | 3/2020 | Cousins |
| 10,595,716 B2 | 3/2020 | Nazareth |
| 10,601,950 B2 | 3/2020 | Devam et al. |
| 10,603,113 B2 | 3/2020 | Lang |
| 10,603,133 B2 | 3/2020 | Wang et al. |
| 10,606,085 B2 | 3/2020 | Toyama |
| 10,594,998 B1 | 4/2020 | Casas |
| 10,610,172 B2 | 4/2020 | Hummel et al. |
| 10,610,179 B2 | 4/2020 | Altmann |
| 10,613,352 B2 | 4/2020 | Knoll |
| 10,617,566 B2 | 4/2020 | Esmonde |
| 10,620,460 B2 | 4/2020 | Carabin |
| 10,625,099 B2 | 4/2020 | Takahashi |
| 10,626,473 B2 | 4/2020 | Mariani |
| 10,631,905 B2 | 4/2020 | Asfora et al. |
| 10,631,907 B2 | 4/2020 | Zucker |
| 10,634,331 B1 | 4/2020 | Feinbloom |
| 10,638,080 B2 | 4/2020 | Ovchinnikov |
| 10,646,285 B2 | 5/2020 | Siemionow et al. |
| 10,650,513 B2 | 5/2020 | Penney et al. |
| 10,650,594 B2 | 5/2020 | Jones |
| 10,652,525 B2 | 5/2020 | Woods |
| 10,660,715 B2 | 5/2020 | Dozeman |
| 10,663,738 B2 | 5/2020 | Carlvik |
| 10,682,112 B2 | 6/2020 | Pizaine |
| 10,682,767 B2 | 6/2020 | Grafenberg et al. |
| 10,687,901 B2 | 6/2020 | Thomas |
| 10,691,397 B1 | 6/2020 | Clements |
| 10,702,713 B2 | 7/2020 | Mori |
| 10,709,398 B2 | 7/2020 | Schweizer |
| 10,713,801 B2 | 7/2020 | Jordan |
| 10,716,643 B2 | 7/2020 | Justin et al. |
| 10,722,733 B2 | 7/2020 | Takahashi |
| 10,725,535 B2 | 7/2020 | Yu |
| 10,731,832 B2 | 8/2020 | Koo |
| 10,732,721 B1 | 8/2020 | Clements |
| 10,742,949 B2 | 8/2020 | Casas |
| 10,743,939 B1 | 8/2020 | Lang |
| 10,747,315 B2 | 8/2020 | Tungare |
| 10,777,094 B1 | 9/2020 | Rao |
| 10,777,315 B2 | 9/2020 | Zehavi |
| 10,781,482 B2 | 9/2020 | Gubatayao |
| 10,792,110 B2 | 10/2020 | Eung et al. |
| 10,799,145 B2 | 10/2020 | West et al. |
| 10,799,296 B2 | 10/2020 | Lang |
| 10,799,316 B2 | 10/2020 | Sela et al. |
| 10,810,799 B2 | 10/2020 | Tepper et al. |
| 10,818,019 B2 | 10/2020 | Piat |
| 10,818,101 B2 | 10/2020 | Gallop et al. |
| 10,818,199 B2 | 10/2020 | Buras et al. |
| 10,825,563 B2 | 11/2020 | Gibby et al. |
| 10,831,943 B2 | 11/2020 | Santarone |
| 10,835,296 B2 | 11/2020 | Elimelech et al. |
| 10,838,206 B2 | 11/2020 | Fortin-Deschnes et al. |
| 10,839,629 B2 | 11/2020 | Jones |
| 10,839,956 B2 | 11/2020 | Beydoun et al. |
| 10,841,556 B2 | 11/2020 | Casas |
| 10,842,002 B2 | 11/2020 | Chang |
| 10,842,461 B2 | 11/2020 | Johnson et al. |
| 10,849,691 B2 | 12/2020 | Zucker |
| 10,849,693 B2 | 12/2020 | Lang |
| 10,849,710 B2 | 12/2020 | Liu |
| 10,861,236 B2 | 12/2020 | Geri et al. |
| 10,865,220 B2 | 12/2020 | Ebetino |
| 10,869,517 B1 | 12/2020 | Halpern |
| 10,869,727 B2 | 12/2020 | Yanof et al. |
| 10,872,472 B2 | 12/2020 | Watola |
| 10,877,262 B1 | 12/2020 | Luxembourg |
| 10,877,296 B2 | 12/2020 | Lindsey |
| 10,878,639 B2 | 12/2020 | Douglas |
| 10,893,260 B2 | 1/2021 | Trail et al. |
| 10,895,742 B2 | 1/2021 | Schneider |
| 10,895,743 B2 | 1/2021 | Dausmann |
| 10,895,906 B2 | 1/2021 | West et al. |
| 10,898,151 B2 | 1/2021 | Harding et al. |
| 10,921,595 B2 | 2/2021 | Rakshit |
| 10,928,321 B2 | 2/2021 | Rawle |

(56) References Cited

U.S. PATENT DOCUMENTS

| | | |
|---|---|---|
| 10,928,638 B2 | 2/2021 | Ninan |
| 10,935,815 B1 | 3/2021 | Castaneda |
| 10,935,816 B2 | 3/2021 | Ban |
| 10,936,537 B2 | 3/2021 | Huston |
| 10,939,973 B2 | 3/2021 | DiMaio |
| 10,939,977 B2 | 3/2021 | Messinger et al. |
| 10,941,933 B2 | 3/2021 | Ferguson |
| 10,946,108 B2 | 3/2021 | Zhang |
| 10,950,338 B2 | 3/2021 | Douglas |
| 10,951,872 B2 | 3/2021 | Casas |
| 10,964,095 B1 | 3/2021 | Douglas |
| 10,964,124 B1 | 3/2021 | Douglas |
| 10,966,768 B2 | 4/2021 | Poulos |
| 10,993,754 B2 | 5/2021 | Kuntz et al. |
| 11,000,335 B2 | 5/2021 | Dorman |
| 11,006,093 B1 | 5/2021 | Hegyi |
| 11,013,560 B2 | 5/2021 | Lang |
| 11,013,562 B2 | 5/2021 | Marti |
| 11,013,573 B2 | 5/2021 | Chang |
| 11,013,900 B2 | 5/2021 | Malek |
| 11,019,988 B2 | 6/2021 | Fiebel |
| 11,027,027 B2 | 6/2021 | Manning |
| 11,029,147 B2 | 6/2021 | Abovitz et al. |
| 11,030,809 B2 | 6/2021 | Wang |
| 11,041,173 B2 | 6/2021 | Zhang |
| 11,045,663 B2 | 6/2021 | Mori |
| 11,049,293 B2 | 6/2021 | Chae |
| 11,049,476 B2 | 6/2021 | Fuchs et al. |
| 11,050,990 B2 | 6/2021 | Casas |
| 11,057,505 B2 | 7/2021 | Dharmatilleke |
| 11,058,390 B1 | 7/2021 | Douglas |
| 11,061,257 B1 | 7/2021 | Hakim |
| 11,065,062 B2 | 7/2021 | Frushour |
| 11,067,387 B2 | 7/2021 | Marell |
| 11,071,497 B2 | 7/2021 | Hallack |
| 11,079,596 B2 | 8/2021 | Hua et al. |
| 11,087,039 B2 | 8/2021 | Duff |
| 11,090,019 B2 | 8/2021 | Siemionow et al. |
| 11,097,129 B2 | 8/2021 | Sakata |
| 11,099,376 B1 | 8/2021 | Steier |
| 11,103,320 B2 | 8/2021 | LeBoeuf |
| D930,162 S | 9/2021 | Cremer et al. |
| 11,109,762 B1 | 9/2021 | Steier |
| 11,122,164 B2 | 9/2021 | Gigante |
| 11,123,604 B2 | 9/2021 | Fung |
| 11,129,562 B2 | 9/2021 | Roberts et al. |
| 11,132,055 B2 | 9/2021 | Jones et al. |
| 11,135,015 B2 | 10/2021 | Crawford |
| 11,135,016 B2 | 10/2021 | Frielinghaus et al. |
| 11,141,221 B2 | 10/2021 | Hobeika |
| 11,153,549 B2 | 10/2021 | Casas |
| 11,153,555 B1 | 11/2021 | Healy et al. |
| 11,163,176 B2 | 11/2021 | Karafin |
| 11,164,324 B2 | 11/2021 | Liu |
| 11,166,006 B2 | 11/2021 | Hegyi |
| 11,172,990 B2 | 11/2021 | Lang |
| 11,179,136 B2 | 11/2021 | Kohli |
| 11,180,557 B2 | 11/2021 | Noelle |
| 11,185,891 B2 | 11/2021 | Cousins |
| 11,202,682 B2 | 12/2021 | Staunton |
| 11,207,150 B2 | 12/2021 | Healy |
| 11,217,028 B2 | 1/2022 | Jones |
| 11,224,763 B2 | 1/2022 | Takahashi |
| 11,227,417 B2 | 1/2022 | Berlinger |
| 11,244,508 B2 | 2/2022 | Kazanzides et al. |
| 11,253,216 B2 | 2/2022 | Crawford et al. |
| 11,253,323 B2 | 2/2022 | Hughes et al. |
| 11,257,190 B2 | 2/2022 | Mao |
| 11,263,772 B2 | 3/2022 | Siemionow et al. |
| 11,269,401 B2 | 3/2022 | West et al. |
| 11,272,151 B2 | 3/2022 | Casas |
| 11,278,359 B2 | 3/2022 | Siemionow et al. |
| 11,278,413 B1 | 3/2022 | Lang |
| 11,280,480 B2 | 3/2022 | Wilt |
| 11,284,846 B2 | 3/2022 | Graumann |
| 11,311,341 B2 | 3/2022 | Lang |
| 11,291,521 B2 | 4/2022 | Im |
| 11,294,167 B2 | 4/2022 | Ishimoda |
| 11,297,285 B2 | 4/2022 | Pierce |
| 11,300,252 B2 | 4/2022 | Nguyen |
| 11,300,790 B2 | 4/2022 | Cheng et al. |
| 11,304,759 B2 | 4/2022 | Kovtun et al. |
| 11,307,402 B2 | 4/2022 | Steier |
| 11,317,973 B2 | 5/2022 | Calloway |
| 11,337,763 B2 | 5/2022 | Choi |
| 11,348,257 B2 | 5/2022 | Lang |
| 11,350,072 B1 | 5/2022 | Casas |
| 11,350,965 B2 | 6/2022 | Yilmaz et al. |
| 11,351,006 B2 | 6/2022 | Aferzon |
| 11,360,315 B2 | 6/2022 | Tu |
| 11,382,699 B2 | 7/2022 | Wassall |
| 11,382,700 B2 | 7/2022 | Calloway |
| 11,382,712 B2 | 7/2022 | Elimelech et al. |
| 11,382,713 B2 | 7/2022 | Healy |
| 11,389,252 B2 | 7/2022 | Gera et al. |
| 11,432,828 B1 | 9/2022 | Lang |
| 11,432,931 B2 | 9/2022 | Lang |
| 11,452,568 B2 | 9/2022 | Lang |
| 11,460,915 B2 | 10/2022 | Frielinghaus |
| 11,461,983 B2 | 10/2022 | Jones |
| 11,464,581 B2 | 10/2022 | Calloway |
| 11,483,532 B2 | 10/2022 | Casas |
| 11,490,986 B2 | 11/2022 | Ben-Yishai |
| 2002/0082498 A1 | 6/2002 | Wendt et al. |
| 2003/0117393 A1 | 6/2003 | Sauer et al. |
| 2003/0130576 A1 | 7/2003 | Seeley |
| 2003/0156144 A1 | 8/2003 | Morita |
| 2003/0210812 A1 | 11/2003 | Khamene et al. |
| 2004/0030237 A1 | 2/2004 | Lee et al. |
| 2004/0138556 A1 | 7/2004 | Cosman |
| 2005/0017972 A1 | 1/2005 | Poole |
| 2005/0024586 A1 | 2/2005 | Tiewes et al. |
| 2005/0119639 A1 | 6/2005 | McCombs et al. |
| 2005/0203367 A1 | 9/2005 | Ahmed et al. |
| 2005/0215879 A1 | 9/2005 | Chuanggui |
| 2006/0134198 A1 | 6/2006 | Tawa |
| 2006/0176242 A1 | 8/2006 | Jaramaz et al. |
| 2007/0018975 A1 | 1/2007 | Chaunggui et al. |
| 2007/0183041 A1 | 8/2007 | McCloy et al. |
| 2008/0007645 A1 | 1/2008 | McCutchen |
| 2008/0085033 A1 | 4/2008 | Haven et al. |
| 2008/0159612 A1 | 7/2008 | Fu |
| 2008/0183065 A1 | 7/2008 | Goldbach |
| 2008/0221625 A1 | 9/2008 | Hufner et al. |
| 2008/0253527 A1 | 10/2008 | Boyden et al. |
| 2008/0262812 A1 | 10/2008 | Arata et al. |
| 2009/0018437 A1 | 1/2009 | Cooke |
| 2009/0062869 A1 | 3/2009 | Claverie et al. |
| 2009/0099445 A1 | 4/2009 | Burger |
| 2009/0036902 A1 | 5/2009 | Dimaio et al. |
| 2009/0227847 A1 | 9/2009 | Tepper et al. |
| 2009/0300540 A1 | 12/2009 | Russell |
| 2010/0114110 A1 | 5/2010 | Taft et al. |
| 2010/0149073 A1 | 6/2010 | Chaum et al. |
| 2010/0210939 A1 | 8/2010 | Hartmann et al. |
| 2011/0004259 A1 | 1/2011 | Stallings et al. |
| 2011/0098553 A1 | 4/2011 | Robbins et al. |
| 2011/0105895 A1 | 5/2011 | Kornblau et al. |
| 2011/0216060 A1 | 9/2011 | Weising et al. |
| 2011/0245625 A1 | 10/2011 | Trovato et al. |
| 2011/0248064 A1 | 10/2011 | Marczyk |
| 2011/0254922 A1 | 10/2011 | Schaerer et al. |
| 2011/0306873 A1 | 12/2011 | Shenai et al. |
| 2012/0014608 A1 | 1/2012 | Watanabe |
| 2012/0068913 A1 | 3/2012 | Bar-Zeev et al. |
| 2012/0078236 A1 | 3/2012 | Schoepp |
| 2012/0109151 A1 | 5/2012 | Maier-Hein et al. |
| 2012/0143050 A1 | 6/2012 | Heigl |
| 2012/0155064 A1 | 6/2012 | Waters |
| 2012/0182605 A1 | 7/2012 | Hall et al. |
| 2012/0216411 A1 | 8/2012 | Wevers et al. |
| 2012/0289777 A1 | 11/2012 | Chopra et al. |
| 2012/0306850 A1 | 12/2012 | Balan et al. |
| 2012/0320100 A1 | 12/2012 | Malchida et al. |

(56) References Cited

U.S. PATENT DOCUMENTS

| | | |
|---|---|---|
| 2013/0002928 A1 | 1/2013 | Imai |
| 2013/0009853 A1 | 1/2013 | Hesselink et al. |
| 2013/0050258 A1 | 2/2013 | Liu et al. |
| 2013/0050833 A1 | 2/2013 | Lewis et al. |
| 2013/0057581 A1 | 3/2013 | Meier |
| 2013/0083009 A1 | 4/2013 | Geisner et al. |
| 2013/0106833 A1 | 5/2013 | Fun |
| 2013/0135734 A1 | 5/2013 | Shaffer et al. |
| 2013/0190602 A1 | 7/2013 | Liao |
| 2013/0209953 A1 | 8/2013 | Arlinsky et al. |
| 2013/0234914 A1 | 9/2013 | Fujimaki |
| 2013/0234935 A1 | 9/2013 | Griffith |
| 2013/0237811 A1 | 9/2013 | Mihailescu et al. |
| 2013/0249787 A1 | 9/2013 | Morimoto |
| 2013/0249945 A1 | 9/2013 | Kobayashi |
| 2013/0265623 A1 | 10/2013 | Sugiyama |
| 2013/0267838 A1 | 10/2013 | Fronk et al. |
| 2013/0278635 A1 | 10/2013 | Maggiore |
| 2013/0300760 A1 | 11/2013 | Sugano et al. |
| 2013/0342571 A1 | 12/2013 | Kinnebrew et al. |
| 2014/0031668 A1 | 1/2014 | Mobasser et al. |
| 2014/0049629 A1 | 2/2014 | Siewerdsen et al. |
| 2014/0088402 A1 | 3/2014 | Xu |
| 2014/0088990 A1 | 3/2014 | Nawana et al. |
| 2014/0104505 A1 | 4/2014 | Koenig |
| 2014/0114173 A1 | 4/2014 | Bar-Tal et al. |
| 2014/0142426 A1 | 5/2014 | Razzaque et al. |
| 2014/0168261 A1 | 6/2014 | Margolis et al. |
| 2014/0176661 A1 | 6/2014 | Smurro et al. |
| 2014/0177023 A1 | 6/2014 | Gao et al. |
| 2014/0189508 A1 | 7/2014 | Granchi et al. |
| 2014/0198129 A1 | 7/2014 | Liu et al. |
| 2014/0240484 A1 | 8/2014 | Kodama et al. |
| 2014/0243614 A1 | 8/2014 | Rothberg et al. |
| 2014/0256429 A1 | 9/2014 | Kobayashi et al. |
| 2014/0266983 A1 | 9/2014 | Christensen |
| 2014/0268356 A1 | 9/2014 | Bolas et al. |
| 2014/0270505 A1 | 9/2014 | McCarthy |
| 2014/0285404 A1 | 9/2014 | Takano et al. |
| 2014/0285429 A1 | 9/2014 | Simmons |
| 2014/0300632 A1 | 10/2014 | Laor |
| 2014/0300967 A1 | 10/2014 | Tilleman et al. |
| 2014/0303491 A1 | 10/2014 | Shekhar et al. |
| 2014/0320399 A1 | 10/2014 | Kim et al. |
| 2014/0333899 A1 | 11/2014 | Smithwick |
| 2014/0336461 A1 | 11/2014 | Reiter et al. |
| 2014/0340286 A1 | 11/2014 | Machida et al. |
| 2014/0361956 A1 | 12/2014 | Mikhailov et al. |
| 2015/0005772 A1 | 1/2015 | Anglin et al. |
| 2015/0018672 A1 | 1/2015 | Blumhofer et al. |
| 2015/0070347 A1 | 3/2015 | Hoffman et al. |
| 2015/0084990 A1 | 3/2015 | Labor |
| 2015/0150641 A1 | 6/2015 | Daon et al. |
| 2015/0209119 A1 | 7/2015 | Theodore et al. |
| 2015/0261922 A1 | 9/2015 | Nawana et al. |
| 2015/0277123 A1 | 10/2015 | Chaum et al. |
| 2015/0282735 A1 | 10/2015 | Rossner |
| 2015/0287188 A1 | 10/2015 | Gazit |
| 2015/0287236 A1 | 10/2015 | Winn |
| 2015/0297314 A1 | 10/2015 | Fowler et al. |
| 2015/0305828 A1 | 10/2015 | Park et al. |
| 2015/0310668 A1 | 10/2015 | Ellerbrock |
| 2015/0350517 A1 | 12/2015 | Duret et al. |
| 2015/0351863 A1 | 12/2015 | Plassky et al. |
| 2015/0363978 A1 | 12/2015 | Maimone et al. |
| 2015/0366620 A1 | 12/2015 | Cameron et al. |
| 2016/0022287 A1 | 1/2016 | Nehls |
| 2016/0030131 A1 | 2/2016 | Yang et al. |
| 2016/0086380 A1 | 3/2016 | Vayser et al. |
| 2016/0103318 A1 | 4/2016 | Du et al. |
| 2016/0125603 A1 | 5/2016 | Tanji |
| 2016/0133051 A1 | 5/2016 | Aonuma et al. |
| 2016/0143699 A1* | 5/2016 | Tanji ............... A61B 34/20 600/431 |
| 2016/0153004 A1 | 6/2016 | Zhang |
| 2016/0175064 A1 | 6/2016 | Steinle et al. |
| 2016/0178910 A1 | 6/2016 | Giudicelli et al. |
| 2016/0191887 A1 | 6/2016 | Casas |
| 2016/0223822 A1 | 8/2016 | Harrison et al. |
| 2016/0228033 A1 | 8/2016 | Rossner |
| 2016/0256223 A1 | 9/2016 | Haimerl et al. |
| 2016/0302870 A1 | 10/2016 | Wilkinson et al. |
| 2016/0324580 A1 | 11/2016 | Esterberg |
| 2016/0324583 A1 | 11/2016 | Kheradpir et al. |
| 2016/0339337 A1 | 11/2016 | Ellsworth et al. |
| 2017/0014119 A1 | 1/2017 | Capote et al. |
| 2017/0027650 A1 | 2/2017 | Merck et al. |
| 2017/0031163 A1 | 2/2017 | Gao et al. |
| 2017/0068119 A1 | 3/2017 | Antaki |
| 2017/0076501 A1 | 3/2017 | Jagga et al. |
| 2017/0086941 A1 | 3/2017 | Marti et al. |
| 2017/0112586 A1 | 4/2017 | Dhupar |
| 2017/0164919 A1 | 6/2017 | Avallee et al. |
| 2017/0164920 A1 | 6/2017 | Lavallee et al. |
| 2017/0220224 A1 | 8/2017 | Kodali |
| 2017/0239015 A1 | 8/2017 | Sela et al. |
| 2017/0251900 A1 | 9/2017 | Hansen et al. |
| 2017/0252109 A1 | 9/2017 | Yang et al. |
| 2017/0281283 A1 | 10/2017 | Siegler et al. |
| 2017/0312032 A1 | 11/2017 | Amanatullah et al. |
| 2017/0348055 A1 | 12/2017 | Salcedo et al. |
| 2017/0348061 A1 | 12/2017 | Joshi et al. |
| 2017/0367766 A1 | 12/2017 | Mahfouz |
| 2017/0367771 A1 | 12/2017 | Tako et al. |
| 2017/0372477 A1 | 12/2017 | Penne |
| 2018/0003981 A1 | 1/2018 | Urey |
| 2018/0018791 A1* | 1/2018 | Guoyi ............... G06T 7/80 |
| 2018/0028266 A1 | 2/2018 | Barnes et al. |
| 2018/0036884 A1 | 2/2018 | Chen et al. |
| 2018/0049622 A1 | 2/2018 | Ryan et al. |
| 2018/0055579 A1 | 3/2018 | Daon et al. |
| 2018/0078316 A1 | 3/2018 | Schaewe et al. |
| 2018/0082480 A1 | 3/2018 | White et al. |
| 2018/0092667 A1 | 4/2018 | Heigl et al. |
| 2018/0092698 A1 | 4/2018 | Chopra et al. |
| 2018/0092699 A1 | 4/2018 | Finley |
| 2018/0116732 A1 | 5/2018 | Lin et al. |
| 2018/0117150 A1 | 5/2018 | O'Dwyer |
| 2018/0133871 A1 | 5/2018 | Farmer |
| 2018/0153626 A1 | 6/2018 | Yang et al. |
| 2018/0185100 A1 | 7/2018 | Weinstein et al. |
| 2018/0193097 A1 | 7/2018 | McLahlin et al. |
| 2018/0200002 A1 | 7/2018 | Kostrzewski et al. |
| 2018/0247128 A1 | 8/2018 | Alvi et al. |
| 2018/0262743 A1 | 9/2018 | Casas |
| 2018/0311011 A1 | 11/2018 | Van Beek et al. |
| 2018/0317803 A1 | 11/2018 | Ben-Yishai et al. |
| 2018/0318035 A1 | 11/2018 | McLahlin et al. |
| 2018/0368898 A1 | 12/2018 | DiVincenzo et al. |
| 2019/0000372 A1 | 1/2019 | Gullotti et al. |
| 2019/0000564 A1 | 1/2019 | Navab et al. |
| 2019/0015163 A1 | 1/2019 | Abhari et al. |
| 2019/0038362 A1 | 2/2019 | Nash et al. |
| 2019/0038365 A1 | 2/2019 | Soper |
| 2019/0046272 A1 | 2/2019 | Zoabi et al. |
| 2019/0046276 A1 | 2/2019 | Inglese et al. |
| 2019/0053851 A1 | 2/2019 | Siemionow et al. |
| 2019/0069971 A1 | 3/2019 | Tripathi et al. |
| 2019/0080515 A1 | 3/2019 | Geri |
| 2019/0105116 A1 | 4/2019 | Johnson et al. |
| 2019/0130792 A1 | 5/2019 | Rios |
| 2019/0142519 A1 | 5/2019 | Siemionow et al. |
| 2019/0144443 A1 | 5/2019 | Jackson |
| 2019/0192230 A1 | 6/2019 | Siemionow et al. |
| 2019/0201106 A1 | 7/2019 | Siemionow et al. |
| 2019/0216537 A1 | 7/2019 | Eltorai |
| 2019/0254753 A1 | 8/2019 | Johnson |
| 2019/0273916 A1 | 9/2019 | Benishti et al. |
| 2019/0333480 A1 | 10/2019 | Lang |
| 2019/0369717 A1 | 12/2019 | Frielinghaus |
| 2019/0387351 A1 | 12/2019 | Lyren |
| 2020/0019364 A1 | 1/2020 | Pond |
| 2020/0020249 A1 | 1/2020 | Jarc et al. |
| 2020/0038112 A1 | 2/2020 | Amanatullah et al. |

(56) References Cited

U.S. PATENT DOCUMENTS

| | | |
|---|---|---|
| 2020/0078100 A1 | 3/2020 | Weinstein et al. |
| 2020/0085511 A1 | 3/2020 | Oezbek et al. |
| 2020/0088997 A1 | 3/2020 | Lee |
| 2020/0159313 A1 | 3/2020 | Gibby et al. |
| 2020/0100847 A1 | 4/2020 | Siegler et al. |
| 2020/0117025 A1 | 4/2020 | Sauer |
| 2020/0129058 A1 | 4/2020 | Li |
| 2020/0129136 A1 | 4/2020 | Harding et al. |
| 2020/0129262 A1 | 4/2020 | Verard |
| 2020/0129264 A1 | 4/2020 | Dativia et al. |
| 2020/0133029 A1 | 4/2020 | Yonezawa |
| 2020/0138518 A1 | 5/2020 | Lang |
| 2020/0138618 A1 | 5/2020 | Roszkowiak et al. |
| 2020/0143594 A1 | 5/2020 | Lal et al. |
| 2020/0146546 A1 | 5/2020 | Chene |
| 2020/0151507 A1 | 5/2020 | Siemionow et al. |
| 2020/0156259 A1 | 5/2020 | Morales |
| 2020/0163723 A1 | 5/2020 | Wolf et al. |
| 2020/0184638 A1 | 6/2020 | Meglan |
| 2020/0186786 A1 | 6/2020 | Gibby et al. |
| 2020/0188028 A1 | 6/2020 | Feiner et al. |
| 2020/0188034 A1 | 6/2020 | LeQuette et al. |
| 2020/0201082 A1 | 6/2020 | Carabin |
| 2020/0229877 A1 | 7/2020 | Siemionow et al. |
| 2020/0237256 A1 | 7/2020 | Farshad et al. |
| 2020/0237459 A1 | 7/2020 | Racheli et al. |
| 2020/0237880 A1 | 7/2020 | Kent |
| 2020/0242280 A1 | 7/2020 | Pavloff et al. |
| 2020/0246074 A1 | 8/2020 | Lang |
| 2020/0246081 A1 | 8/2020 | Johnson et al. |
| 2020/0265273 A1 | 8/2020 | Wei |
| 2020/0275988 A1 | 9/2020 | Johnson |
| 2020/0286222 A1 | 9/2020 | Essenreiter et al. |
| 2020/0288075 A1 | 9/2020 | Bonin et al. |
| 2020/0305980 A1 | 10/2020 | Lang |
| 2020/0315734 A1 | 10/2020 | El Amm |
| 2020/0323460 A1 | 10/2020 | Busza |
| 2020/0327721 A1 | 10/2020 | Siemionow et al. |
| 2020/0330179 A1 | 10/2020 | Ton |
| 2020/0337780 A1 | 10/2020 | Winkler et al. |
| 2020/0341283 A1 | 10/2020 | McCracken |
| 2020/0352655 A1* | 11/2020 | Freese .................. G06T 11/00 |
| 2020/0355927 A1 | 11/2020 | Marcellin-Dibon |
| 2020/0360091 A1 | 11/2020 | Murray et al. |
| 2020/0375666 A1 | 12/2020 | Murphy |
| 2020/0377493 A1 | 12/2020 | Heiser |
| 2020/0377956 A1 | 12/2020 | Vogelstein |
| 2020/0389425 A1 | 12/2020 | Bhatia |
| 2020/0390502 A1 | 12/2020 | Holthuizen et al. |
| 2020/0390503 A1 | 12/2020 | Casas et al. |
| 2020/0402647 A1 | 12/2020 | Domracheva |
| 2020/0409306 A1 | 12/2020 | Gelman et al. |
| 2020/0410687 A1 | 12/2020 | Siemionow et al. |
| 2020/0413031 A1 | 12/2020 | Khani |
| 2021/0004956 A1 | 1/2021 | Book et al. |
| 2021/0009339 A1 | 1/2021 | Morrison et al. |
| 2021/0015583 A1 | 1/2021 | Avisar |
| 2021/0022599 A1 | 1/2021 | Freeman et al. |
| 2021/0022808 A1 | 1/2021 | Lang |
| 2021/0022811 A1 | 1/2021 | Mahfouz |
| 2021/0022828 A1 | 1/2021 | Elimelech et al. |
| 2021/0029804 A1 | 1/2021 | Chang |
| 2021/0030374 A1 | 2/2021 | Takahashi |
| 2021/0030511 A1 | 2/2021 | Wolf et al. |
| 2021/0038339 A1 | 2/2021 | Yu |
| 2021/0049825 A1 | 2/2021 | Wheelwright et al. |
| 2021/0052348 A1 | 2/2021 | Stifter et al. |
| 2021/0065911 A1 | 3/2021 | Goel et al. |
| 2021/0077195 A1 | 3/2021 | Saeidi |
| 2021/0077210 A1 | 3/2021 | Itkowitz |
| 2021/0080751 A1 | 3/2021 | Lindsey |
| 2021/0090344 A1 | 3/2021 | Geri et al. |
| 2021/0093391 A1 | 4/2021 | Poltaretskyi et al. |
| 2021/0093392 A1 | 4/2021 | Poltaretskyi et al. |
| 2021/0093400 A1 | 4/2021 | Quid et al. |
| 2021/0093417 A1 | 4/2021 | Liu |
| 2021/0104055 A1 | 4/2021 | Ni et al. |
| 2021/0107923 A1 | 4/2021 | Jackson |
| 2021/0109349 A1 | 4/2021 | Schneider |
| 2021/0109373 A1 | 4/2021 | Loo |
| 2021/0110517 A1 | 4/2021 | Flohr |
| 2021/0113269 A1 | 4/2021 | Vilsmeier |
| 2021/0113293 A9 | 4/2021 | Silva et al. |
| 2021/0121238 A1 | 4/2021 | Palushi et al. |
| 2021/0137634 A1 | 5/2021 | Lang et al. |
| 2021/0141887 A1 | 5/2021 | Kim et al. |
| 2021/0150702 A1 | 5/2021 | Claessen |
| 2021/0157544 A1 | 5/2021 | Denton |
| 2021/0160472 A1 | 5/2021 | Casas |
| 2021/0161614 A1 | 6/2021 | Elimelech et al. |
| 2021/0162287 A1 | 6/2021 | Xing |
| 2021/0165207 A1 | 6/2021 | Peyman |
| 2021/0169504 A1 | 6/2021 | Brown |
| 2021/0169578 A1 | 6/2021 | Calloway et al. |
| 2021/0169581 A1 | 6/2021 | Calloway et al. |
| 2021/0169605 A1 | 6/2021 | Calloway et al. |
| 2021/0196404 A1 | 7/2021 | Wang |
| 2021/0223577 A1 | 7/2021 | Zheng |
| 2021/0227791 A1 | 7/2021 | De Oliveira Seixas |
| 2021/0235061 A1 | 7/2021 | Hegyi |
| 2021/0248822 A1 | 8/2021 | Choi |
| 2021/0282887 A1 | 9/2021 | Wiggermann |
| 2021/0290046 A1 | 9/2021 | Nazareth |
| 2021/0290336 A1 | 9/2021 | Wang |
| 2021/0290394 A1 | 9/2021 | Mahfouz |
| 2021/0295512 A1 | 9/2021 | Knoplioch |
| 2021/0298835 A1 | 9/2021 | Wang |
| 2021/0306599 A1 | 9/2021 | Pierce |
| 2021/0311322 A1 | 10/2021 | Belanger |
| 2021/0314502 A1 | 10/2021 | Liu |
| 2021/0315636 A1 | 10/2021 | Akbarian |
| 2021/0315662 A1 | 10/2021 | Freeman et al. |
| 2021/0325684 A1 | 10/2021 | Ninan |
| 2021/0333561 A1 | 10/2021 | Oh |
| 2021/0346115 A1 | 11/2021 | Dulin et al. |
| 2021/0349677 A1 | 11/2021 | Baldev |
| 2021/0369226 A1 | 12/2021 | Siemionow et al. |
| 2021/0371413 A1 | 12/2021 | Thurston |
| 2021/0373333 A1 | 12/2021 | Moon |
| 2021/0373344 A1 | 12/2021 | Loyola |
| 2021/0378757 A1 | 12/2021 | Bay |
| 2021/0389590 A1 | 12/2021 | Freeman |
| 2021/0400247 A1 | 12/2021 | Casas |
| 2021/0401533 A1 | 12/2021 | Im |
| 2021/0402255 A1 | 12/2021 | Fung |
| 2021/0405369 A1 | 12/2021 | King |
| 2022/0003992 A1 | 1/2022 | Ahn |
| 2022/0007006 A1 | 1/2022 | Healy et al. |
| 2022/0008135 A1 | 1/2022 | Frielinghaus et al. |
| 2022/0038675 A1 | 2/2022 | Hegyi |
| 2022/0039873 A1 | 2/2022 | Harris |
| 2022/0051484 A1 | 2/2022 | Jones et al. |
| 2022/0071712 A1 | 3/2022 | Wolf et al. |
| 2022/0079675 A1 | 3/2022 | Lang |
| 2022/0121041 A1 | 4/2022 | Hakim |
| 2022/0142730 A1 | 5/2022 | Wolf et al. |
| 2022/0155861 A1 | 5/2022 | Myung |
| 2022/0159227 A1 | 5/2022 | Quiles Casas |
| 2022/0179209 A1 | 6/2022 | Cherukuri |
| 2022/0192776 A1 | 6/2022 | Gibby et al. |
| 2022/0201274 A1 | 6/2022 | Achilefu et al. |
| 2022/0245400 A1 | 8/2022 | Siemionow et al. |
| 2022/0133484 A1 | 9/2022 | Lang |
| 2022/0287676 A1 | 9/2022 | Steines et al. |
| 2022/0295033 A1 | 9/2022 | Casas |
| 2022/0358759 A1 | 11/2022 | Cork et al. |
| 2022/0405935 A1 | 12/2022 | Flossmann et al. |
| 2023/0009793 A1 | 1/2023 | Gera et al. |

(56) References Cited

U.S. PATENT DOCUMENTS

| | | |
|---|---|---|
| 2023/0027801 A1 | 1/2023 | Qian et al. |
| 2023/0034189 A1 | 2/2023 | Gera et al. |

FOREIGN PATENT DOCUMENTS

| | | |
|---|---|---|
| CN | 101379412 A | 3/2009 |
| CN | 103106348 A | 5/2013 |
| CN | 111915696 A | 11/2020 |
| CN | 112489047 A | 3/2021 |
| DE | 202004011567 U1 | 11/2004 |
| DE | 102014008153 A1 | 10/2014 |
| EP | 0933096 A2 | 8/1999 |
| EP | 1640750 A | 3/2006 |
| EP | 1757974 A1 | 2/2007 |
| EP | 2134847 B1 | 6/2015 |
| EP | 2891966 B1 | 1/2017 |
| EP | 3123970 A1 | 2/2017 |
| EP | 2654749 B1 | 5/2017 |
| EP | 3216416 A1 | 9/2017 |
| EP | 2032039 B1 | 10/2017 |
| EP | 3247297 A1 | 11/2017 |
| EP | 2030193 B1 | 7/2018 |
| EP | 3034607 B1 | 3/2019 |
| EP | 2892558 B1 | 4/2019 |
| EP | 2635299 B1 | 7/2019 |
| EP | 3505050 A1 | 7/2019 |
| EP | 3224376 B1 | 8/2019 |
| EP | 2875149 B1 | 12/2019 |
| EP | 3206583 B1 | 9/2020 |
| EP | 2625845 B1 | 3/2021 |
| EP | 3076660 B1 | 4/2021 |
| EP | 3858280 A1 | 8/2021 |
| EP | 3593227 B1 | 9/2021 |
| EP | 3789965 B1 | 12/2021 |
| EP | 3634294 B1 | 1/2022 |
| EP | 3952331 A1 | 2/2022 |
| GB | 2507314 A | 4/2014 |
| KR | 10-2014-0120155 A | 10/2014 |
| WO | 03034705 A2 | 4/2003 |
| WO | 2007/051304 A1 | 5/2007 |
| WO | 2007115826 A2 | 10/2007 |
| WO | 2008103383 A1 | 8/2008 |
| WO | 2010067267 A1 | 6/2010 |
| WO | WO2010074747 A1 | 7/2010 |
| WO | WO2012101286 A1 | 8/2012 |
| WO | 2013112554 A1 | 8/2013 |
| WO | 2014024188 A1 | 2/2014 |
| WO | WO2014037953 A2 | 3/2014 |
| WO | 2014113455 A1 | 7/2014 |
| WO | 2014125789 A1 | 8/2014 |
| WO | 2014167563 A1 | 10/2014 |
| WO | 2014174067 A1 | 10/2014 |
| WO | 2015058816 A1 | 4/2015 |
| WO | WO2015061752 A1 | 4/2015 |
| WO | WO2015109145 A1 | 7/2015 |
| WO | 2016151506 A1 | 9/2016 |
| WO | WO2007115826 A2 | 10/2017 |
| WO | 2018/052966 A1 | 3/2018 |
| WO | 2018/073452 A1 | 4/2018 |
| WO | WO2018200767 A1 | 4/2018 |
| WO | 2018206086 A1 | 11/2018 |
| WO | 2019/083431 A1 | 5/2019 |
| WO | 2019/161477 A1 | 8/2019 |
| WO | 2019195926 A1 | 10/2019 |
| WO | 2019/211741 A1 | 11/2019 |
| WO | WO2019210353 A1 | 11/2019 |
| WO | 2020109903 A1 | 6/2020 |
| WO | 2020109904 A1 | 6/2020 |
| WO | 2021019369 A1 | 2/2021 |
| WO | WO2021017019 A1 | 2/2021 |
| WO | WO2021023574 A1 | 2/2021 |
| WO | WO2021046455 A1 | 3/2021 |
| WO | WO2021048158 A1 | 3/2021 |
| WO | WO2021021979 A2 | 4/2021 |
| WO | WO2021061459 A1 | 4/2021 |
| WO | WO2021062375 A1 | 4/2021 |
| WO | WO2021073743 A1 | 4/2021 |
| WO | WO2021087439 A1 | 5/2021 |
| WO | WO2021091980 A1 | 5/2021 |
| WO | 2021255627 A1 | 6/2021 |
| WO | WO2021112918 A1 | 6/2021 |
| WO | 2021130564 A1 | 7/2021 |
| WO | WO2021137752 A1 | 7/2021 |
| WO | WO2021141887 A1 | 7/2021 |
| WO | WO2021145584 A1 | 7/2021 |
| WO | WO2021154076 A1 | 8/2021 |
| WO | 2021/188757 A1 | 9/2021 |
| WO | WO2021183318 A2 | 12/2021 |
| WO | WO2021257897 A1 | 12/2021 |
| WO | WO2021258078 A1 | 12/2021 |
| WO | WO2022009233 A1 | 1/2022 |
| WO | 2022053923 A1 | 3/2022 |
| WO | 2022079565 A1 | 4/2022 |
| WO | 2023/281395 A1 | 1/2023 |
| WO | 2023/007418 A1 | 2/2023 |
| WO | 2023/021448 A1 | 2/2023 |
| WO | 2023/021450 A1 | 2/2023 |
| WO | 2023/021451 A1 | 2/2023 |
| WO | 2023/026229 A1 | 3/2023 |

OTHER PUBLICATIONS

Webster (ed.), "Structured Light Techniques and Applications," Wiley Encyclopedia of Electrical and Electronics Engineering, pp. 1-24, year 2016.

Liberadzki et al., "Structured-Light-Based System for Shape Measurement of the Human Body in Motion," Sensors, vol. 18, pp. 1-19, year 2018.

Romero, "Volume Ray Casting Techniques and Applications Using General Purpose Computations on Graphics Processing Units," Thesis/Dissertation Collections, Rochester Institute of Technology, RIT Scholar Works, pp. 1-140, Jun. 2009.

Zhang et al., "Medical Volume Rendering Techniques," Independent Research, Spring 2014, arXiv:1802.07710v1, pp. 1-33, Feb. 21, 2018.

Van Ooijen et al., "Noninvasive Coronary Imaging Using Electron Beam CT: Surface Rendering Versus Volume Rendering," Computers in Radiology, AJR, vol. 180, pp. 223-226, Jan. 2003.

Fingas., "Fraunhofer iPad app guides liver surgery through augmented reality", pp. 1-6, Aug. 22, 2013.

Hainich et al., "Near-Eye displays", Chapter 10 of Displays: Fundamentals and Applications, CRC press, pp. 439-504, Jul. 5, 2011.

Lumus Ltd., "DK-32 See-through Wearable Display Development Kit", Rehovot, Israel, pp. 1-2, Dec. 24, 2013.

BrainLab—Image Registration Options Enhanced Visualization Leveraging More Data, pp. 1-4, Feb. 2019.

Gera et al., U.S. Appl. No. 17/388,064, filed Jul. 29, 2021.

International Application PCT/IB2022/056986 filed Jul. 28, 2022.
International Application PCT/IB2022/057733 filed Aug. 18, 2022.
International Application PCT/IB2022/057735 filed Aug. 18, 2022.
International Application PCT/IB2022/057736 filed Aug. 18, 2022.
International Application PCT/IB2022/057965 filed Aug. 25, 2022.
International Application PCT/IB2022/059030 filed Sep. 23, 2022.
International Application PCT/IB2022/056212 filed Jul. 5, 2022.

Mitrasinovic et al., "Clinical and surgical applications of smart glasses", pp. 381-401, Technology and Health Care, issue 23, year 2015.

Martin-Gonzalez et al., "Head-mounted virtual loupe with sight-based activation for surgical applications", IEEE symposium on mixed and augmented reality, pp. 207-208, Oct. 19-22, 2009.

Figl et al., "A fully automated calibration method for an optical see-through head-mounted operating microscope with variable zoom and focus", pp. 1492-1499, IEEE transactions on medical imaging, vol. 24, No. 11, Nov. 2005.

Medithinq Co. Ltd., "Metascope: world's first wearable scope", pp. 1-7, Jan. 2023.

Martin-Gonzalez et al., "Sight-based magnification system for surgical applications", pp. 26-30, Conference proceedings of Bildverarbeitung für die Medizin, year 2010.

(56) References Cited

OTHER PUBLICATIONS

Burstrom et al., "Frameless patient tracking with adhesive optical skin markers for augmented reality surgical navigation in spine surgery", Spine, vol. 45, No. 22, pp. 1598-1604, year 2020.
Suenaga et al., "Vision-based markerless registration using stereo vision and an augmented reality surgical navigation system: a pilot study", BMC Medical Imaging, pp. 1-11, year 2015.
Mayfield Clinic, "Spinal Fusion: Lateral Lumbar Interbody Fusion (LLIF)", pp. 1-6, Jan. 2021.
Qian et al., "AR-Loupe: Magnified Augmented Reality by Combining an Optical See-Through Head-Mounted Display and a Loupe", pp. 2550-2562, IEEE Transactions on Visualization and Computer Graphics, vol. 28, No. 7, Jul. 2022.
Kazanzides et al., "Systems and Methods for Augmented Reality Magnifying Loupe", case ID 15944, pp. 1-2, Nov. 26, 2020.
EP Application # 19891059.8 Search Report dated Jul. 27, 2022.
EP Application # 19890849.3 Search Report dated Jul. 27, 2022.
U.S. Appl. No. 16/419,023 Office Action dated Sep. 1, 2022.
U.S. Appl. No. 16/524,258 Office Action dated Oct. 24, 2022.
International Application PCT/IB2022/057736 Search report dated Nov. 24, 2022.
U.S. Appl. No. 16/200,144 Office Action dated Nov. 30, 2022.
International Application PCT/IB2022/056986 Search Report dated Dec. 7, 2022.
JP Application # 2021-525186 Office Action dated Aug. 23, 2022.
International Application PCT/IB2022/057965 Search Report dated Dec. 15, 2022.
U.S. Appl. No. 16/524,258 Office Action dated Jan. 24, 2023.
International Application PCT/IB2022/057733 Search Report dated Jan. 26, 2023.
European Application 22203956.2 Search Report dated Feb. 9, 2023.
International Application PCT/IB2022/059030 Search report dated Feb. 28, 2023.

\* cited by examiner

MIRRORING IN IMAGE GUIDED SURGERY

CROSS-REFERENCE TO RELATED APPLICATION

This application is a continuation of U.S. patent application Ser. No. 16/724,297, filed Dec. 22, 2019, which is incorporated herein by reference.

FIELD OF THE INVENTION

This invention relates generally to an augmented reality system, and specifically to correct image projection when it is used in image guided surgery.

BACKGROUND

Correct imaging is important in image guided surgery, and a number of systems are known in the art for producing correct imaging.

U.S. Pat. Nos. 7,630,753 and 9,757,087, to Simon et al., describe a surgical instrument navigation system that allows a surgeon to invert the three-dimensional perspective of the instrument to match their perspective of the actual instrument.

U.S. Pat. No. 9,538,962, to Hannaford et al., describes a system for providing networked communications. The system includes a plurality of head-mountable devices, each in communication with a control system via a communication network.

U.S. Pat. No. 9,710,968, to Dillavou et al., describes a system for role designation with multiple sources.

U.S. Pat. No. 9,886,552, to Dillavou et al., describes a method for image registration that includes rendering a common field of interest that reflects a presence of a plurality of elements. At least one of the elements is a remote element located remotely from another of the elements.

U.S. Pat. No. 9,940,750, to Dillavou et al., describes a method for role negotiation that can comprise rendering a common field of interest that reflects a presence of a plurality of elements. At least one of the elements is a remote element located remotely from another of the elements.

U.S. Pat. No. 9,959,629, to Dillavou et al., describes a method for managing spatiotemporal uncertainty in image processing. The method can comprise determining motion from a first image to a second image.

U.S. Pat. No. 10,194,131, to Casas, describes a real-time surgery method for displaying a stereoscopic augmented view of a patient from a static or dynamic viewpoint of the surgeon. The method employs real-time three-dimensional surface reconstruction for preoperative and intraoperative image registration.

US Patent Application 2011/0216060, to Weising et al., describes a method for controlling a view of a virtual scene with a portable device. A signal is received and the portable device is synchronized to make the location of the portable device a reference point in a three-dimensional (3D) space.

US Patent Application 2017/0027650, to Merck et al., describes receiving data characterizing a mother video feed acquired by an endoscopic video capture device. The mother video feed can be for characterizing an operative field within a patient.

US Patent Application 2017/0251900, to Hansen et al., describes a depiction system for generating a real time correlated depiction of movements of a surgical tool for uses in minimally invasive surgery.

US Patent Application 2017/0367771, to Tako et al., describes a virtual reality surgical navigation method that includes a step of receiving data indicative of a surgeon's current head position, including a direction of view and angle of view of the surgeon.

US Patent Application 2018/0247128, to Alvi et al., describes a system for accessing a surgical dataset including surgical data collected during performance of a surgical procedure. The surgical data can include video data of the surgical procedure.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY

An embodiment of the present invention provides an imaging system, consisting of:

a head-mounted display configured to be worn by an operator of the system;

a marker configured to be attached to a human subject and defining a plane when attached to the human subject, the marker having optically reflective elements disposed on the marker and on opposing sides of the plane in a non-symmetrical arrangement with respect to the plane;

a memory configured to store a graphical representation of a tool used in a procedure performed by the operator on the human subject, and an image of anatomy of the human subject;

a camera attached to the display and configured to acquire an input image of the marker and of the tool; and a processor configured to analyze the input image so as to identify the plane and to identify a side of the plane wherein the camera is located, and to render to the display the image of the anatomy of the human subject with the graphical representation of the tool superimposed thereon from a point of view in the identified side of the plane.

In a disclosed embodiment the plane makes an angle between $+20°$ and $-20°$ with a sagittal plane of the human subject. Alternatively, the plane makes an angle between $+20°$ and $-20°$ with an axial plane of the human subject.

In a further disclosed embodiment the marker has a two-dimensional surface which makes an angle between $+20°$ and $-20°$ with a frontal plane of the human subject.

In a yet further disclosed embodiment the marker defines a further plane and the optically reflective elements are disposed on opposing sides of the further plane in a non-symmetrical arrangement with respect to the further plane, and the processor is configured to analyze the input image so as to identify the further plane and to identify a side of the further plane wherein the camera is located, and to render to the display the image of the anatomy of the human subject with the graphical representation of the tool superimposed thereon from a point of view in the identified side of the further plane. Typically, the plane and the further plane are orthogonal to each other.

In an alternative embodiment the camera is located at a vertical height above the marker, and the processor is configured:

to ascertain the vertical height in response to the acquired input image of the marker;

to calculate a pair of planes, each of the pair having a preset acute angle to the identified plane and defining a first acute-angled wedge region and a second acute-angled wedge region to the identified plane; and when the display moves so that the point of view crosses the first acute-angled wedge region and the second acute-angled wedge region, or begins within the first acute-angled wedge region and crosses the second acute-angled wedge region, while the camera remains at the vertical height, to render to the display the image of the anatomy of the human subject with the graphical representation of the tool superimposed thereon from the point of view of a region opposite the identified side.

Typically the preset acute angle is less than or equal to 10°.

In a further alternative embodiment the camera is located at a vertical height above the marker, and the processor is configured:

to ascertain the vertical height in response to the acquired input image of the marker; and when the display moves so that the vertical height changes, to render unchanged to the display the image of the anatomy of the human subject with the graphical representation of the tool superimposed thereon.

There is further provided, according to an embodiment of the present invention, an imaging system, consisting of:

a first head-mounted display configured to be worn by a first operator of the system;

a second head-mounted display configured to be worn by a second operator of the system;

a marker configured to be attached to a human subject and defining a plane when attached to the human subject, the marker having optically reflective elements disposed on the marker and on opposing sides of the plane in a non-symmetrical arrangement with respect to the plane;

a memory configured to store a graphical representation of a tool used in a procedure performed by the first operator on the human subject, and an image of anatomy of the human subject;

a first camera attached to the first display and configured to acquire a first input image of the marker and of the tool;

a second camera attached to the second display and configured to acquire a second input image of the marker and of the tool; and a processor configured to:

analyze the first input image so as to identify the plane and to identify a first side of the plane wherein the first camera is located, and to render to the first display the image of the anatomy of the human subject with the graphical representation of the tool superimposed thereon from a first point of view in the identified first side of the plane, and analyze the second input image so as to identify the plane and to identify a second side of the plane wherein the second camera is located, and to render to the second display the image of the anatomy of the human subject with the graphical representation of the tool superimposed thereon from a second point of view in the identified second side of the plane.

There is further provided, according to an embodiment of the present invention, a method, consisting of:

providing a head-mounted display configured to be worn by an operator of an imaging system;

attaching a marker to a human subject, the marker defining a plane when attached, the marker having optically reflective elements disposed on the marker and on opposing sides of the plane in a non-symmetrical arrangement with respect to the plane;

storing in a memory a graphical representation of a tool used in a procedure performed by the operator on the human subject, and storing an image of anatomy of the human subject in the memory;

attaching a camera to the display;

acquiring an input image of the marker and of the tool with the camera; and analyzing the input image so as to identify the plane and to identify a side of the plane wherein the camera is located, and to render to the display the image of the anatomy of the human subject with the graphical representation of the tool superimposed thereon from a point of view in the identified side of the plane.

The present disclosure will be more fully understood from the following detailed description of the embodiments thereof, taken together with the drawings. A brief description of the drawings follows.

DETAILED DESCRIPTION OF EMBODIMENTS

Overview

Figure 1:
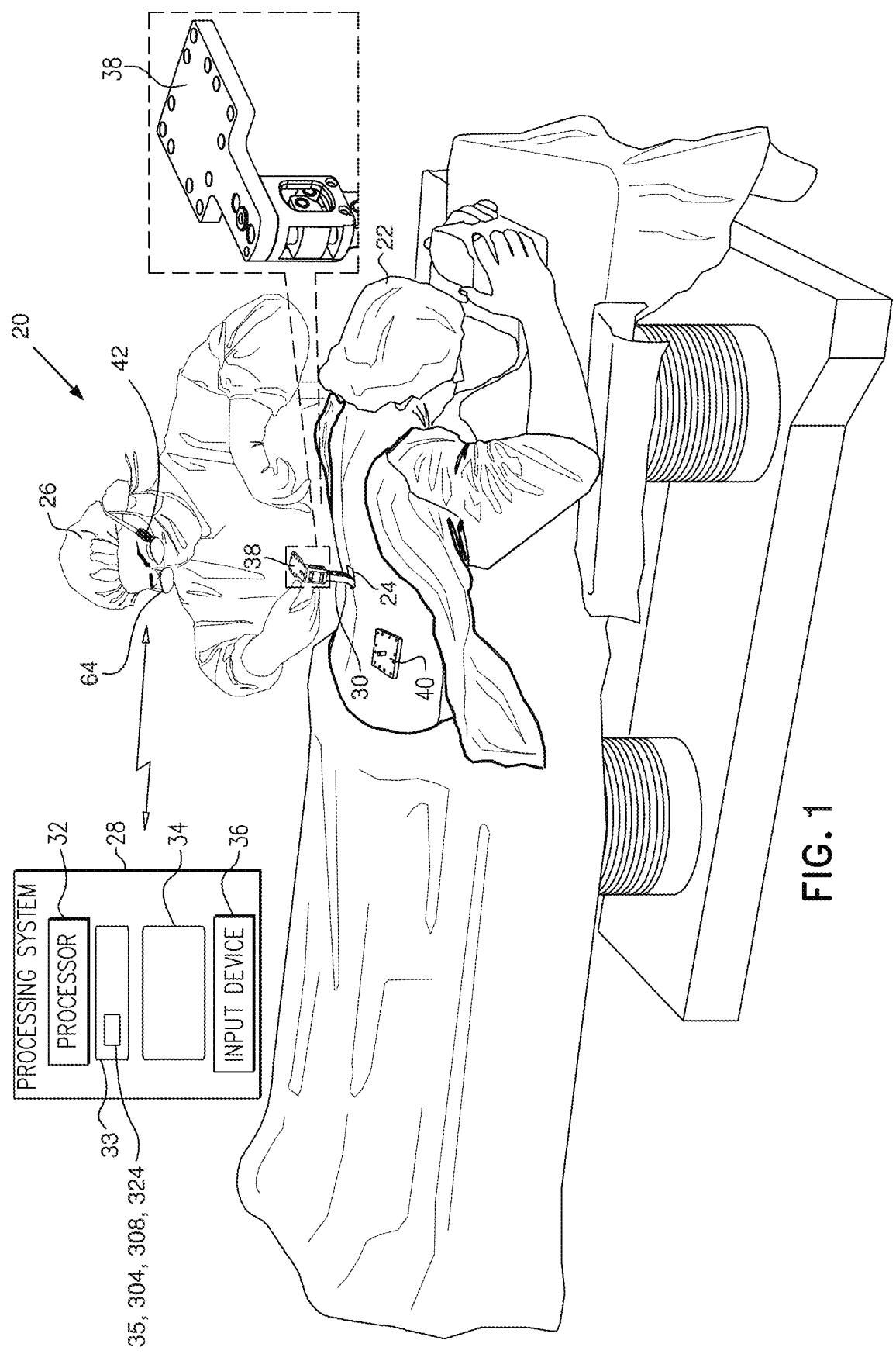
FIG. 1 is a schematic illustration of an initial preparatory stage of a medical procedure, according to an embodiment of the present invention.

A head-mounted display, for a medical procedure that implements an imaging system, such as an augmented reality system, in the display, typically needs to access stored computerized tomography (CT) files of the anatomy of a human subject. The display is worn by an operator of the system, and the accessed files are presented to the operator as scanned planes of the subject in the display. However, for the presentation to be correctly oriented, it is necessary to know the position of the operator with respect to the subject.

Embodiments of the present invention provide an imaging system that determines the operator position automatically, and so displays an image of the patient anatomy, and of a tool used in the procedure, automatically.

In addition to a head-mounted display (HMD) that is worn by an operator of the system, the system comprises a marker that is attached to the human subject. The marker defines a plane of asymmetry when attached to the human subject, since the marker has optically reflective elements disposed on the marker and on opposing sides of the plane in a non-symmetrical arrangement with respect to the plane. The plane of asymmetry is typically approximately parallel to one of the main anatomical planes of the human subject.

In the imaging system a memory stores a graphical representation of a tool used in the procedure performed by the operator, and the memory also stores an image of the anatomy of the human subject. A camera is attached to the HMD, and acquires an input image of the marker and of the tool. A processor analyzes the input image so as to identify the plane and to identify a side of the plane wherein the camera is located. The processor then renders to the display the image of the anatomy of the human subject with the graphical representation of the tool superimposed thereon from a point of view in the identified side of the plane.

Detailed Description

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

In the description, like elements in the drawings are identified by like numerals, and like elements are differentiated as necessary by appending a letter to the identifying numeral.

Figure 3:
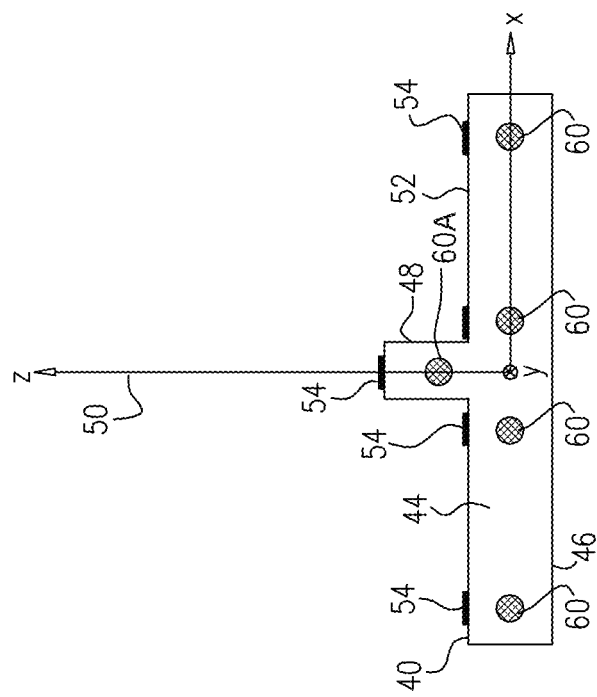
FIGS. 2, 3, and 4 are schematic depictions of entities used in the initial stage, according to an embodiment of the present invention.
Figure 2:
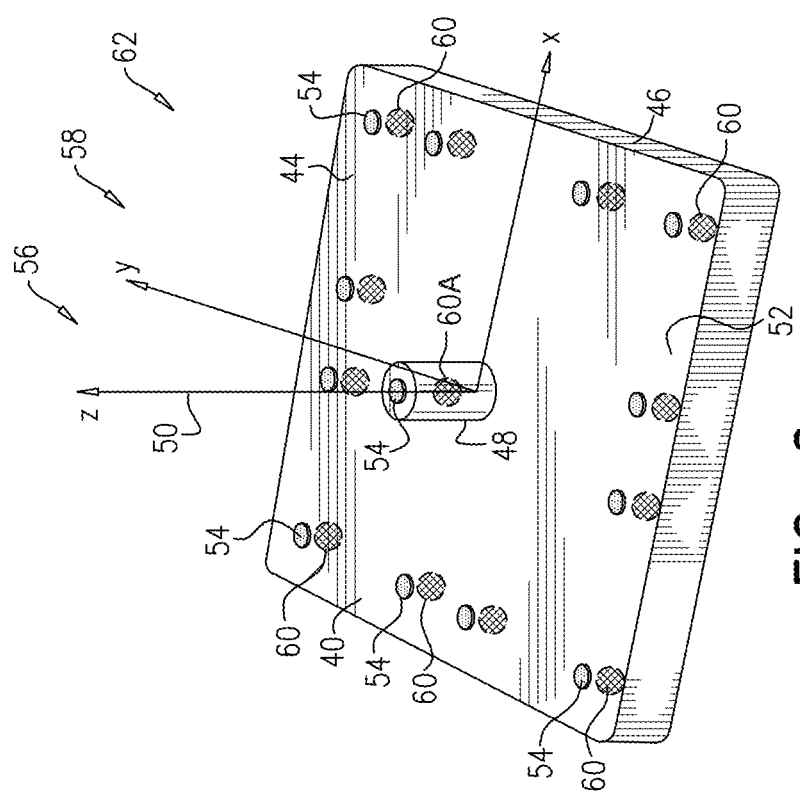
Figure 4:
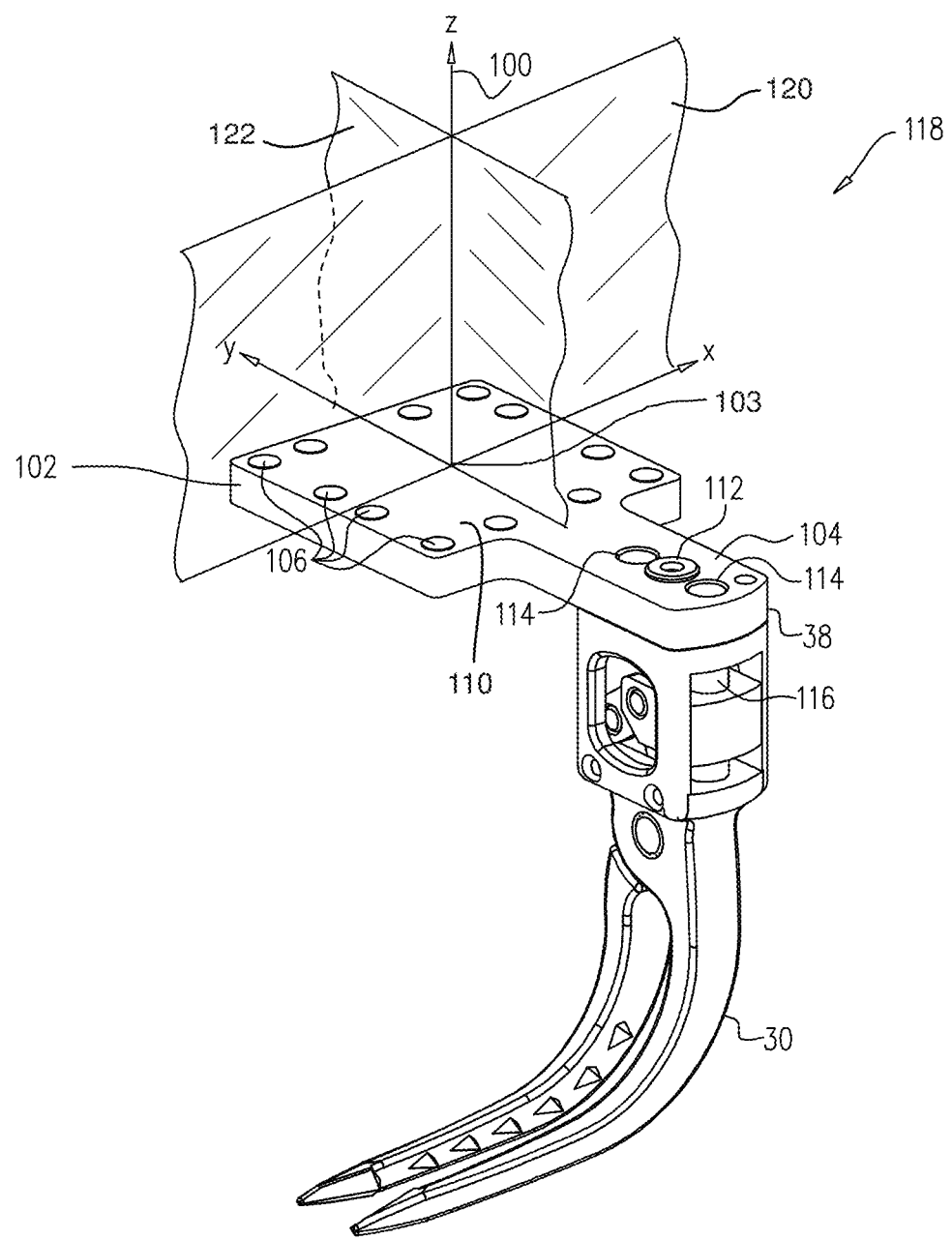

Reference is now made to FIGS. 1, 2, 3, and 4, which are diagrams according to an embodiment of the present invention. FIG. 1 is a schematic illustration of an initial preparatory stage of a medical procedure using an imaging system 20, and FIGS. 2, 3, and 4 are schematic depictions of entities used in the initial stage. The medical procedure exemplified here is performed on the back of a human subject 22, herein also termed patient 22, and during the initial stage of the procedure an operator 26 of system 20, also herein termed medical professional 26 makes an incision 24 into the patient's back. The professional inserts a spinous process clamp 30 into the incision, so that opposing jaws of the clamp are located on opposite sides of the spinous processes. The professional then slides the clamp over the vertebral laminas, and adjusts the clamp to grip one or more spinous processes, selected by the professional, of the patient. Clamp 30 is described below with reference to FIG. 4, and a clamp such as clamp 30 is described in more detail in U.S. Patent Application 2019/0175228 which is incorporated herein by reference.

Clamp 30 acts as a support for a patient marker 38, which is attached rigidly to the clamp. During substantially all of the procedure, i.e., during the initial, as well as the subsequent stages, patient marker 38 is used as a fiducial for patient 30, since because of its rigid connection to the patient, any movement of the patient is reflected in a corresponding motion of the patient marker. In order to operate as such a fiducial, in embodiments of the present invention, in the initial stage of the procedure marker 38 is registered with the anatomy of patient 30, herein assumed to comprise the skeleton of the patient, as is described herein.

During the procedure medical professional 26 wears a head-mounted display (HMD) 64 which is configured to present stored images, that are aligned with patient 22, to professional 26. HMD 64 is described further below.

As is also described below, in serving as a fiducial, marker 38 performs two functions: a first function wherein the marker is used to maintain registration between frames of reference of the head-mounted display and the patient's anatomy, and a second function wherein the marker is used to ascertain where the medical professional is located with respect to the patient. Thus, for the second function, the marker provides a location of the medical professional as being on a left side or a right side of the patient, or on an upper side or a lower side of the patient.

An augmented reality head-mounted display such as HMD 64 is described in more detail in U.S. Patent Application 2017/0178375 which is incorporated herein by reference.

During the initial stage of the procedure, a registration marker 40 is placed on the patient's back, and is used to implement the registration of patient marker 38 with the anatomy of patient 30. In contrast to patient marker 38, registration marker 40 is typically only used during the initial stage of the procedure, i.e., for the registration of the patient marker 38, and once the registration has been performed, for the subsequent procedure stages the registration marker may be removed from the patient's back. As will be apparent from the following description, only registration marker 40 is subject to fluoroscopy, and patient marker 38 is not subject to fluoroscopy.

Also during the initial stage of the procedure, a camera 42, fixedly attached to head-mounted display 64, is used to image the registration marker and the patient marker. Camera 42 typically operates in the visible and/or near-visible spectrum, i.e., at wavelengths of approximately 300 nm-900 nm.

A processing system 28 is coupled, by cables and/or wirelessly, to camera 42. System 28 comprises a computer processor 32, a memory 33 comprising stored images 35 that include images 304, 308, and 324, described below, a screen 34, and an input device 36 such as a pointing device. The system is configured to analyze the images acquired by the camera, as is described further below. Other functions of system 28 are also described below.

In order to operate, HMD 64 is coupled to processor 32 of system 28, or alternatively HMD 64 has its own dedicated processor which performs similar functions to those performed by processor 32. When HMD 64 is operative it presents stored images, that are aligned with patient 22, to professional 26.

FIGS. 2 and 3 are respectively schematic perspective and cross-sectional views of registration marker 40, which is assumed to define a registration marker frame of reference 50, herein assumed to comprise an orthogonal set of xyz axes. Marker 40 is formed from a solid substrate 44, which is opaque to light in the visible and near-visible spectrum, and which is transparent to fluoroscopic radiation. Substrate 44 is typically formed from a hard plastic, such as polycarbonate, but any other solid material which is opaque to light and transparent to fluoroscopic radiation may be used in embodiments of the present invention.

In the illustrated embodiment of marker 40, substrate 44 is formed as a rectangular parallelepiped 46, upon which is mounted a pillar 48.

A plurality of optically reflective, but radiotransparent, discrete elements 54 are disposed on substrate 44. Elements 54 are hereinbelow, by way of example, assumed to comprise discs, and are also referred to herein as discs 54. It is understood that said optically reflective and radiotransparent elements may be of different shapes and/or sizes.

Some of the plurality of discs 54 are fixedly attached, typically by cementing, to a two-dimensional (2D) surface 52 of parallelepiped 46. These discs 54 are formed in a generally rectangular 2D pattern on surface 52. In addition, an optically reflective disc 54 is also cemented onto pillar 48, so that there is in totality a three-dimensional (3D) array of discs 54 disposed on the substrate. The 3D array of discs 54 are distributed on 2D surface 52, and on pillar 48, so that when marker 40 is illuminated and imaged by camera 50 the discs are easily distinguished from substrate 44. Furthermore, as explained in more detail below, the arrangement of discs 54 are configured to enable processor 32 to unambiguously determine the orientation and position of frame of reference 50 from the marker image.

The distributed discs 54 are herein assumed to comprise an optical component 56 of marker 40 that forms an optical pattern 58 for the marker. In a particular aspect of the invention optical pattern 58, comprising the distribution of discs 54, is implemented so that the pattern has no axis of symmetry and no plane of symmetry. The absence of both an axis and a plane of symmetry in the pattern ensures that the unambiguous determination of the orientation and position of the frame of reference of marker 40 is possible from the marker image for multiple different orientations and positions of the marker, the positions being typically within a region approximately 20 cm from the patient marker.

The description above of optical pattern 58 assumes that discs 54 are configured in three dimensions. However, as long as the pattern has no axis of symmetry and no plane of symmetry, the discs forming the pattern may be arranged in only two dimensions, for example, absent the disc on pillar 48. Thus, pattern 58 may be formed in at least two dimensions, i.e., in the case of discs 54, as a two-dimensional array of the discs or as a three-dimensional array of the discs.

It will be understood that the requirement for discs 54 to be arranged to form a pattern having an absence of both an axis and a plane of symmetry may be achieved using discs of substantially the same size and shape, wherein locations of the discs are selected so that the locations are arranged to have the absence of both an axis and a plane of symmetry. The described pattern is hereinbelow referred to as a unique optical pattern.

Alternatively, the unique optical pattern may be achieved using discs of different sizes and/or shapes. In this case, the locations of the discs may also satisfy the requirement, but this is not a necessity.

A multiplicity of radiopaque elements 60 are disposed in substrate 44 by being embedded in a distribution within parallelepiped 46. The distribution of elements 60 is arranged in a two dimensional radiopaque pattern 62 such that, as for the pattern of discs 54, the radiopaque pattern has no axis of symmetry and no plane of symmetry. Because substrate 44 is radiotransparent, and because of the absence of both an axis and a plane of symmetry in radiopaque pattern 62, a fluoroscopic, typically computerized tomography (CT), scan of the radiopaque elements of marker 40 enables the orientation and position of frame of reference 50 to be unambiguously determined by processor 32 from the fluoroscopic scan. In one embodiment elements 60 comprise spheres which are distributed in a 2D generally rectangular 2D pattern that is substantially the same as the rectangular pattern of discs 54 on surface 52.

The description above of elements 60 assumes that they are arranged in a radiopaque pattern of two dimensions. However, as long as the pattern has no axis of symmetry and no plane of symmetry, the elements forming the pattern may also be arranged in three dimensions, for example, by incorporation of a radiopaque element 60A, substantially similar to elements 60, in pillar 48. Thus, pattern 62 may also be formed in at least two dimensions, i.e., in the case of elements 60 and 60A, as a two-dimensional array of elements 60 or as a three-dimensional array of elements 60 and 60A.

As for discs 54, it will be understood that the requirement for elements 60 to be arranged to form a pattern having an absence of both an axis and a plane of symmetry may be achieved using elements of substantially the same size and shape, wherein locations of the elements are selected so that the locations are arranged to have the absence of both an axis and a plane of symmetry. The described pattern is hereinbelow referred to as a unique radiopaque pattern.

Alternatively, the unique radiopaque pattern may be achieved using elements of different sizes and/or shapes. In this case, the locations of the elements may also satisfy the requirement, but this is not a necessity.

The X-ray wavelengths of the CT scan are assumed to be in a range of 0.01-10 nm.

The above description of marker 40 assumes that discs 54 and elements 60 have different functionalities—the discs being optically reflective and radiotransparent, and the elements being radiopaque. In an alternative embodiment of marker 40 at least some of discs 54 are configured to have dual functionality by being optically reflective and radiopaque. As for the embodiment described above, in the alternative embodiment discs 54 are configured and distributed on substrate 44 so that an optical image of marker 40 provides an unambiguous determination of the orientation and position of frame of reference 50, and a fluoroscopic scan of the marker also provides an unambiguous determination of the orientation and position of the frame of reference.

The physical construction of the illustrated embodiment of marker 40, as a pillar attached to a rectangular parallelepiped, comprising an array of discs 54 and an array of elements 60, is but one example of possible physical constructions of the marker that enables an unambiguous determination of the marker's position and orientation from a camera image and from a fluoroscopic scan. In a disclosed embodiment, rather than marker 40 comprising pillar 48 mounted on substrate 44, an indentation (in place of the pillar) is formed within the substrate, and a disc 54 is located on a surface of the indentation.

Other suitable constructions for marker 40 are also considered to be within the scope of the present invention.

For example, the substrate of marker 40, rather than being formed from a parallelepiped with a pillar or an indentation, may be formed as substantially any conveniently shaped solid object that is opaque to light in the visible and near-visible spectrum and which is transparent to fluoroscopic radiation.

In addition, rather than the optical component of marker 40 being comprised of a plurality of discs 54 arranged in a particular pattern, the component may comprise any array or pattern of optical elements that is attached to the substrate, that is diffusely and/or specularly reflective, and that is configured to have the absence of axes and planes of symmetry described above, so that when imaged in visible or near-visible light an unambiguous determination of the marker's position and orientation may be made.

Referring to FIG. 4, patient marker 38 is assumed to define a patient marker frame of reference 100, assumed to comprise an orthogonal set of xyz axes. In the embodiment illustrated in FIG. 4 marker 38 comprises a rectangular parallelepiped substrate 102 to which is attached a tongue 104 used to fixedly connect the substrate to clamp 30. A center 103 of an upper surface of substrate 102 acts as an origin of the xyz axes.

The connection to clamp 30 is by a removable screw 112, and the patient marker connects in a predetermined fixed spatial relationship to the clamp using holes 114 which align with studs 116 of the clamp. Substrate 102 comprises a solid opaque material, and may be formed from any convenient material such as polyimide plastic.

A plurality of optically reflective discs 106, generally similar to discs 54, are attached, typically by cementing, to an upper 2D surface 110 of substrate 102. Discs 106, also referred to herein as reflectors 106, are formed in a generally rectangular 2D pattern on surface 110. Discs 106 are distributed so that when illuminated and imaged by camera 42 they are easily distinguished from substrate 102.

In addition, discs 106 are distributed with respect to an xz plane 120 and a yz plane 122 through origin 103. xz plane 120 and yz plane 122 are planes of asymmetry. Thus, discs 106 are arranged non-symmetrically with respect to xz plane 120, so that the distribution of the discs on one side of plane 120 do not mirror (through the plane) the discs on the opposing side of the plane. In addition, discs 106 are arranged non-symmetrically with respect to yz plane 122, so that the distribution of the discs on one side of plane 122 do not mirror the discs on the opposing side of the plane.

In FIG. 4 discs 106 are shown as being distributed on sides of a rectangle, however, it will be understood that this is but one example for the positioning of the discs on surface 110. Other distributions of discs 106, providing that they define planes of asymmetry as described above, are also assumed to be comprised within the scope of the present invention.

Furthermore, it will be appreciated that the physical construction of patient marker 38 described above is by way of example. Thus, embodiments of the present invention comprise any patient marker formed of any conveniently shaped solid opaque substrate to which is attached an optical pattern, the pattern defining planes of asymmetry as described above.

Figure 5:
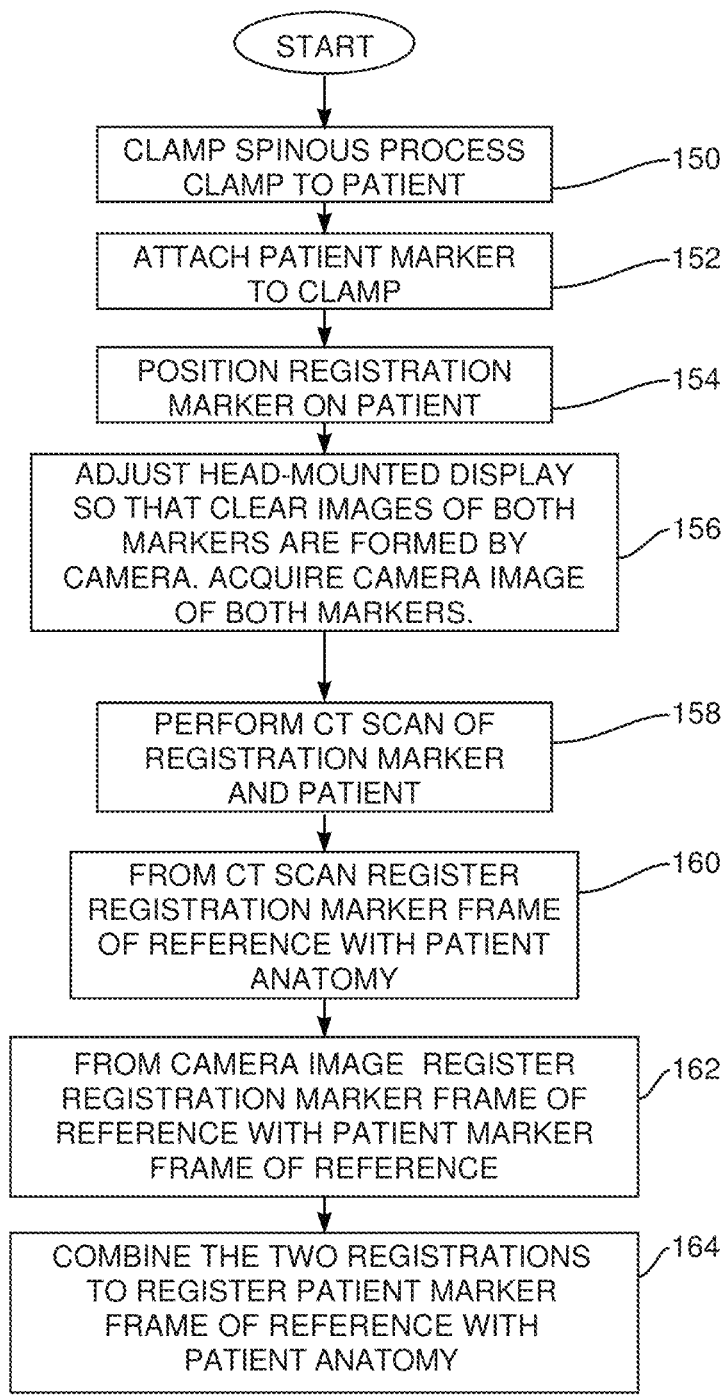
FIG. 5 is a flowchart of steps performed to register a patient marker with the anatomy of a patient during the initial preparatory stage.

FIG. 5 is a flowchart of steps performed to register patient marker 38 with the anatomy of patient 22 during the initial preparatory stage of a medical procedure illustrated in FIG. 1, according to an embodiment of the present invention. While the following description assumes, for simplicity, a CT scan, other types of fluoroscopic imaging are also considered to be within the scope of the present invention.

In an initial step 150, medical professional 26 makes an incision in the back of patient 22, inserts spinous clamp 30 into the patient, and then clamps the clamp to one or more of the processes of the patient.

In a patient marker step 152, the medical professional attaches patient marker 38 to spinous clamp 30, ensuring that the marker is rigidly attached to the clamp. Marker 38 is attached to clamp 30 so that surface 110, corresponding to the xy plane of the xyz axes, is approximately parallel to a frontal plane of patient 22, xz plane of asymmetry 120 is approximately parallel to a sagittal plane of the patient, and so that yz plane of asymmetry 122 is approximately parallel to an axial plane of the patient. As used herein, the term "approximately parallel" as applied to two planes indicates that the planes subtend an angle within a range of ±20° to each other.

In a registration marker step 154, the professional places registration marker 40 on the skin of the back of the patient, typically as close to the patient's spine as is convenient.

In a camera step 156, professional 26 adjusts his/her position so that camera 42, attached to head-mounted display 64 images the registration marker and the patient marker. Professional 26 adjusts their position so that the images formed by camera 42 of the registration marker and of the patient marker are clear images, i.e., that neither marker occludes the other. Typically processor 32 of processing system 28 is configured to verify the acceptability of the two marker images, and if necessary the professional may use and communicate with system 28 to adjust, in an iterative manner, their position and/or that of the registration marker until system 28 provides an indication to the professional that acceptable images are being generated.

Once acceptable images are being generated, a camera image of the two markers is acquired, and is provided to processing system 28.

In a fluoroscopic scan step 158, a CT scan of patient 22, in the vicinity of marker 40 is performed, and processing system 28 acquires the scan. The scan may be performed by inserting patient 22 into a CT scanning system so that marker 40 is scanned. The insertion may be implemented by bringing the CT scanning system to patient 22, or by transporting the patient to the system. In either case, marker 40 remains in the marker's position of step 156.

In a scan analysis step 160, processor 32 analysis the CT scan acquired in step 158, the scan comprising an image of radiopaque elements 60 and of the anatomy of patient 22. From the acquired image, processor 32 calculates the position and orientation of registration marker frame of reference 50, and registers the frame of reference with the anatomy of the patient. The registration typically comprises a set of vectors P between selected points on registration marker 40 and selected vertebrae of patient 22. In one embodiment, the registration comprises using a 4×4 homogenous transformation, comprising a 3×3 rotation and a 1×3 translation, that transforms a point in the space of patient 22 to a point in registration marker frame of reference 50.

In a camera image analysis step 162, processor 32 analyzes the camera image of patient marker 38 and registration marker 40 acquired in step 156. From the acquired image, processor 32 calculates the position and orientation of registration marker frame of reference 50, and the position and orientation of patient marker frame of reference 100. Once the processor has calculated the positions and orientations of the two frames of reference, it formulates a registration of the two frames of reference as a set of vectors Q describing the transformation of the registration marker frame of reference to the patient marker frame of reference.

In a concluding analysis step 164, the processor adds the two sets of vectors found in steps 160 and 162 to formulate a registration set of vectors R between the patient marker frame of reference 36 and the patient anatomy, as shown in equation (1):

$$R = P + Q \qquad (1)$$

Figure 6:
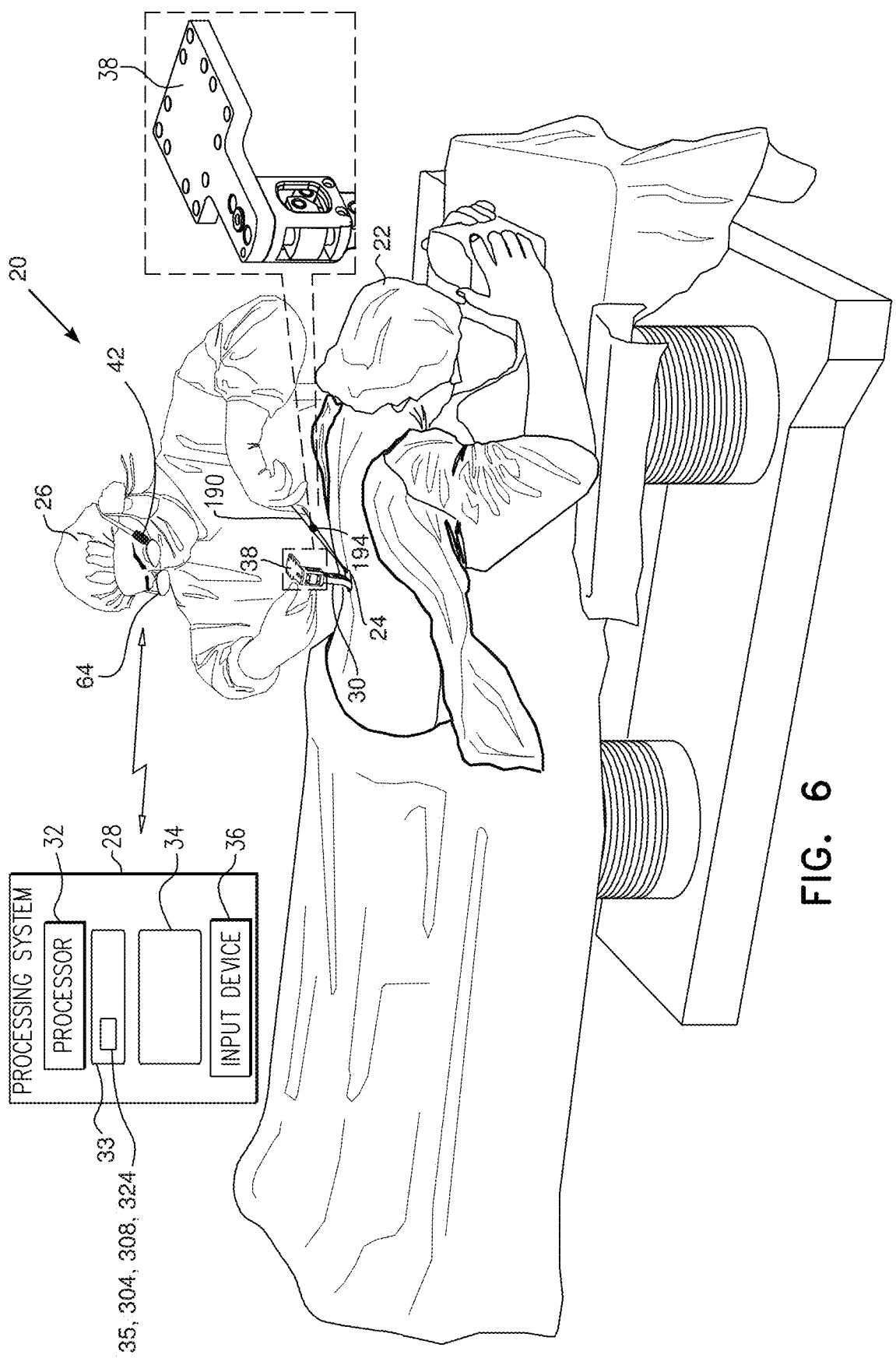
FIG. 6 is a schematic illustration of a subsequent stage of the procedure, according to an embodiment of the present invention.
Figure 7:
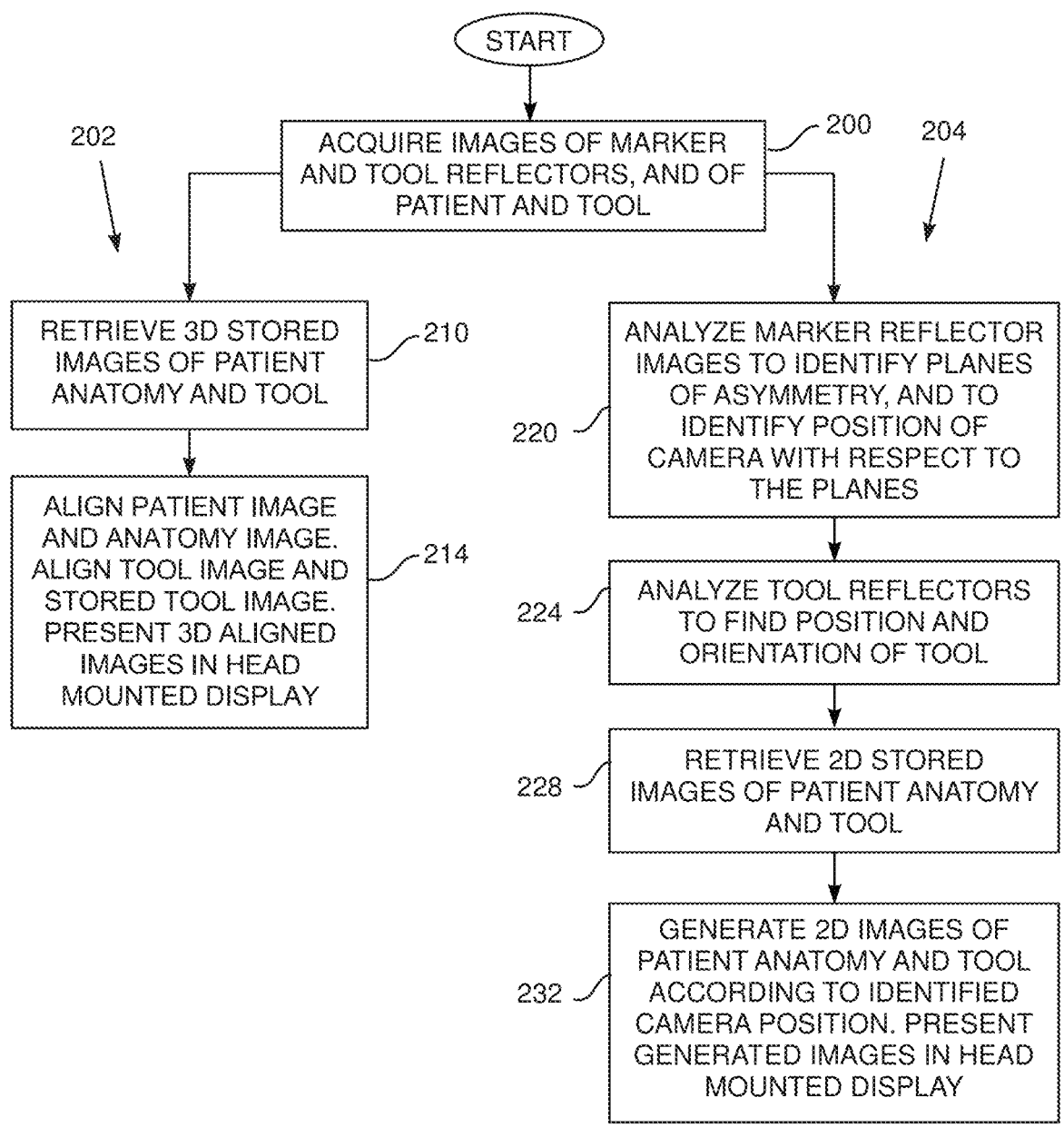
FIG. 7 is a flowchart of steps performed during the subsequent stage, according to an embodiment of the present invention.
Figure 8:
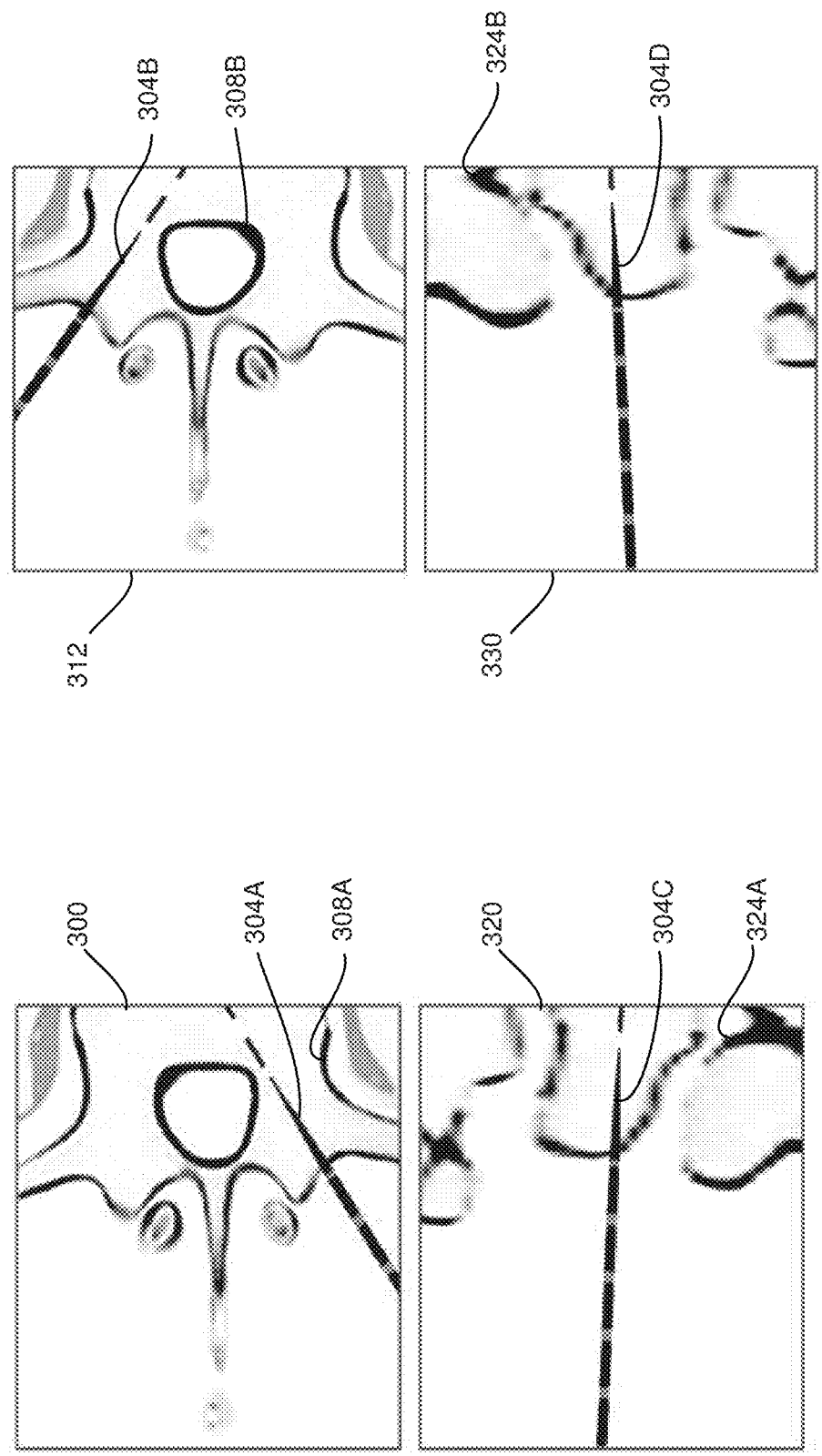
FIG. 8 shows schematic figures illustrating images generated in the subsequent stage, according to an embodiment of the present invention.

FIG. 6 illustrates a subsequent stage of the medical procedure, FIG. 7 is a flowchart of steps performed during the subsequent stage, and FIG. 8 shows schematic figures illustrating images generated in the subsequent stage, according to an embodiment of the present invention. In the subsequent stage registration marker 40 has been removed from the back of patient 22, and medical professional 26 operates on the patient using a surgical tool 190. The tool is tracked by the HMD processor, by having identifying reflectors 194, generally similar to reflectors 106, attached to the tool.

In an initial step 200 of the flowchart of FIG. 7, the HMD projects visible or invisible light to patient marker 38 and tool 190. Camera 42 acquires images of reflectors 106 of the marker, of reflectors 194 of tool 190 and of patient 22 and tool 190.

The flowchart then branches into two paths, a first path 202 and a second path 204. Processor 32 implements steps of both paths substantially simultaneously.

In first path 202, in a three-dimensional (3D) image retrieval step 210, processor 32 retrieves a 3D stored patient anatomy image of patient 22, typically comprising a CT image of the patient, from stored images 35. The processor also retrieves a stored virtual image, also herein termed a stored representation, of tool 190 from the stored images.

In a 3D image presentation step 214, the processor presents aligned 3D images of the patient anatomy and of the virtual tool image in the head mounted display.

The position of the virtual tool image is determined from reflectors 194. In order to ensure that the anatomy image and the virtual tool image, projected by the display, align with the anatomy of patient 22 and with the actual tool image, the processor determines the position and orientation of frame of reference 100 of the patient marker from the acquired images of reflectors 106. The processor applies the registration set of vectors R, found in step 164 of the flowchart of FIG. 5, to the position and orientation of the marker frame of reference, so as to effect the alignment.

In second path 204, in a plane identification step 220, processor 32 analyzes the images of reflectors 106 acquired by camera 42 to identify the position and orientation of xz plane of asymmetry 120 and yz plane of asymmetry 122. From the images the processor also calculates and stores the height of camera 42 above the xy plane.

From the identified positions and orientations of the planes the processor determines on which side of the planes camera 42 resides. Each plane has two sides, and it will be understood that the two planes divide the volume around marker 38 into four regions, the camera residing in one of four regions.

In a tool reflector step 224 the processor analyzes the images of reflectors 194 to find the position and orientation of tool 190.

In an image retrieval step 228 the processor retrieves a stored virtual image of the tool. The processor also retrieves, from the stored 2D images, images of the patient anatomy at the tool position, and parallel to the axial and sagittal planes of the patient.

In an image presentation step 232, the processor uses the retrieved images to generate a combined image of the patient anatomy with a representation of the tool superimposed on the patient anatomy, from a point of view of the camera, i.e., from a point of view in the plane sides identified in step 220.

The processor presents the combined image in HMD 64 for viewing by professional 26.

By presenting images in HMD 64 according to the point of view of camera 42, embodiments of the present invention present correctly oriented images to operator 26, who is wearing the HMD. It will also be understood that the correct orientation is determined according to the position of the operator 26 with respect to the patient, i.e., whether the operator is to the left or right of the patient, and whether the operator is on a lower or upper side of the patient.

FIG. 8 shows schematic illustrations of images generated in step 232, according to an embodiment of the present invention.

A diagram 300 illustrates an image 304A of tool 190 superimposed on an image 308A of the patient anatomy, from a point of view in a left side of a sagittal plane of patient 22, and a diagram 312 illustrates an image 304B of tool 190 superimposed on an image 308B of the patient anatomy, from a point of view in a right side of the patient sagittal plane. The two diagrams are mirror images of each other, and use a stored image 304 of tool 190. The two diagrams also use a stored image 308 of the patient anatomy that is parallel to the patient sagittal plane at an identified position of tool 190.

A diagram 320 illustrates an image 304C of tool 190 superimposed on an image 324A of the patient anatomy, from a point of view in a lower side of an axial plane of patient 22, and a diagram 330 illustrates an image 304D of tool 190 superimposed on an image 324B of the patient anatomy, from a point of view in an upper side of the patient axial plane. As for diagrams 300, 312, the two diagrams 320, 330 are mirror images of each other, and use stored image 304 of tool 190. Diagrams 320, 330 use a stored image 324 of the patient anatomy that is parallel to the patient axial plane at the identified position of tool 190.

Returning to the flowchart of FIG. 7, it will be appreciated that professional 26 may select which images, referred to in steps 214 and 232, are rendered for viewing in the head-mounted display. Thus the professional may view either the 3D images of step 214, or the 2D images of step 232, or both images simultaneously.

Figure 9:
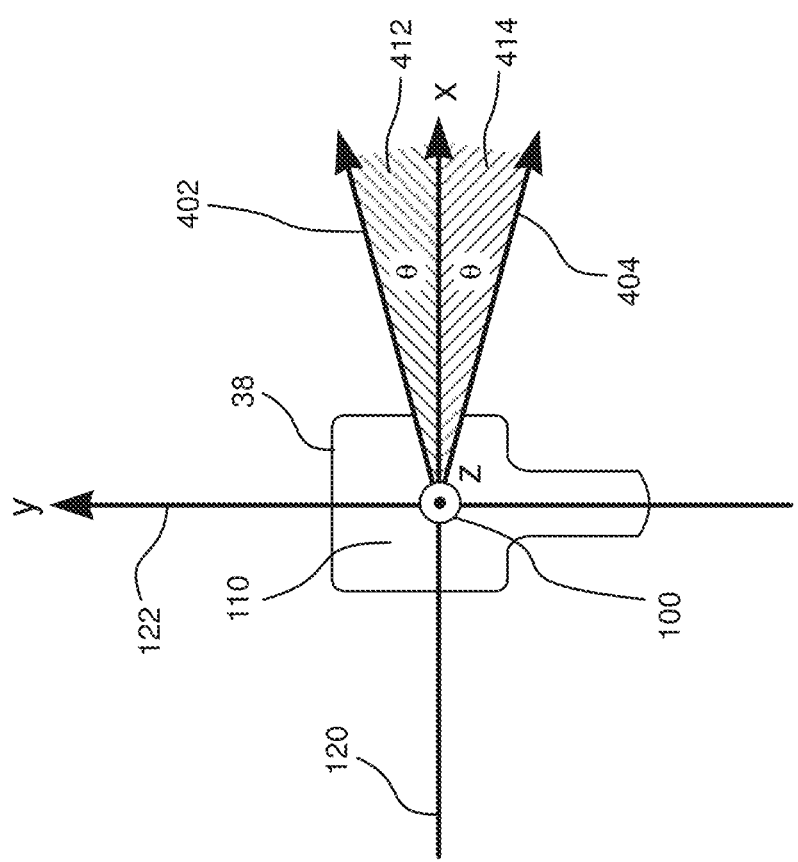
FIG. 9 is a schematic top-down view of a surface of a marker used in the procedure.

FIG. 9 is a schematic top-down view of surface 110 of marker 38, showing the x, y, and z axes of the marker, as well as xz plane 120 and yz plane 122.

As operator 26 moves from one side of xz plane 120 to the other side, then following on from step 232 of the flowchart of FIG. 7 together with the diagrams of FIG. 8, the images presented to the operator are mirror images of each other. The mirroring is also true when the operator moves from one side of yz plane 122 to the other side.

A disclosed embodiment of the present invention places a limitation on the mirroring described above when moving from one side of a plane to another, in order to reduce jitter in the presented images when the operator is close to the plane. In order to reduce jitter, the processor constructs transition regions around xz plane 120 and other transition regions around yz plane 122. The following description is for the transition region around xz plane 120 and to the right of yz plane 122.

Processor 32 constructs a first plane 402 containing and terminating at the z axis, and at an angle +θ from xz plane 120, and a second plane 404 containing and terminating at the z axis, and at −θ from xz plane 120. In one embodiment θ≤10°. The two planes form respective wedge-shaped regions 412, 414 with xz plane 120, and these two wedge-shaped regions comprise the transition region around xz plane 120 and to the right of yz plane 122.

If the movement across xz plane 120 includes both wedge-shaped regions being crossed, by the HMD and the attached camera of the operator, or begins from within one of the wedge-shaped regions and crosses the other one, then the mirroring as described above is implemented.

However, if the movement across the xz plane does not comply with the movements above, e.g., the movement only crosses one wedge-shaped region and stops in the other region, or only moves between wedge-shaped regions, then no mirroring is implemented.

For a transition region around xz plane 120 and to the left of yz plane 122, the processor constructs two planes making angles γθ with the xz plane, generally similar to planes 402 and 404, so as to form two more wedge-shaped regions terminating at the z axis and to the left of the yz plane.

The processor constructs the same type of transition regions for yz plane 122. Thus, for a transition region around yz plane 122 and above xz plane 120, the processor constructs two planes making angles γθ with the yz plane, generally similar to planes 402 and 404, so as to form two wedge-shaped regions terminating at the z axis and above the xz plane.

Similarly, for a transition region around yz plane 122 and below the xz plane, the processor constructs two planes making angles ±θ with the yz plane, generally similar to planes 402 and 404, so as to form two wedge-shaped regions terminating at the z axis and below the xz plane.

There are thus a total of four transition regions distributed symmetrically about the z-axis, each transition region comprising two wedge-shaped regions.

As for the movement for the illustrated transition region, if movement across either of planes 120 or 122 includes both wedge-shaped regions being crossed, by the HMD and the attached camera of the operator, or begins from within one of the wedge-shaped regions and crosses the other one, then the mirroring is implemented.

However, if the movement across either of the planes does not comply with the movements above, then no mirroring is implemented, i.e., mirroring is precluded.

Another disclosed embodiment of the present invention places another limitation on the mirroring described above. In this embodiment, when the operator moves to look over patient 22, mirroring is also precluded. To preclude mirroring for this embodiment, the processor checks if the camera height, measured in step 220 of the flowchart of FIG. 7 has changed, as is the case if operator 26 moves her/his head to look over patient 22. I.e., if the camera height changes, no mirroring is implemented regardless of whether the xz plane or the yz plane have been crossed.

Figure 10:
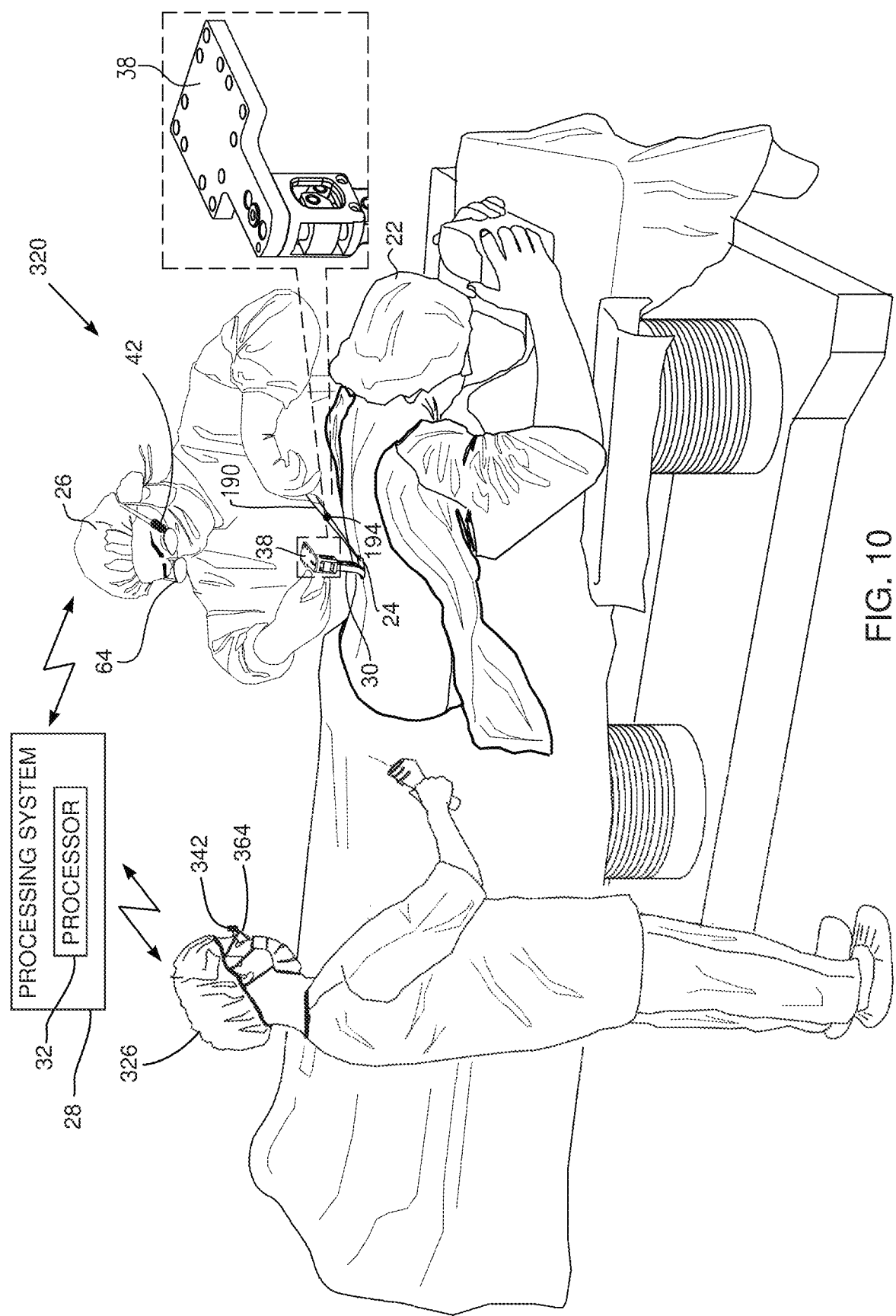
FIG. 10 is a schematic illustration of the subsequent stage of the procedure when there are two operators for the procedure, according to an embodiment of the present invention.

FIG. 10 is a schematic illustration of the subsequent stage of the procedure, when two operators use an imaging system 320, according to an embodiment of the present invention. Apart from the differences described below, the operation of system 320 is generally similar to that of system 20 (FIGS. 1-9), and elements indicated by the same reference numerals in both systems 20 and 320 are generally similar in construction and in function.

In contrast to system 20, system 320 is used by operator 26 and a second operator 326. Second operator 326 wears an HMD 364, and a camera 342 is fixedly attached to the HMD. HMD 364 and camera 342 are respectively substantially similar in construction and function to HMD 64 and camera 42. However, camera 342 is typically not used to perform the registration described in the flowchart of FIG. 5, since this is provided by camera 42.

Images generated in HMD 364 are substantially as described in the flowchart of FIG. 7. Thus, images presented in HMD 364 are oriented according to the point of view of camera 342, i.e., according to whether operator 326 is to the left or right of patient 22, and according to whether the operator is on the lower or upper side of the patient.

It will be understood that by presenting images in a head-mounted display according to the point of view of the camera attached to the display, embodiments of the present invention present correctly oriented images to a wearer of the head-mounted display. It will also be understood that the correct orientation is determined according to the position of the wearer of the HMD with respect to the patient, i.e., whether the wearer is to the left or right of the patient, and whether the wearer is on a lower or upper side of the patient.

It will be further understood that for cases where there is more than one HMD, each being worn by a respective wearer, embodiments of the present invention operate simultaneously and independently to present correctly oriented images to each wearer, according to the position of the respective wearer with respect to the patient. A wearer on the right side of the patient and a wearer on the left side of the patient are presented with mirror images based on anatomy images parallel to the patient sagittal plane; similarly a wearer on the lower side of the patient and a wearer on the upper side of the patient are presented with mirror images based on anatomy images parallel to the patient axial plane.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A computer-implemented method, comprising:
    storing in a memory a graphical representation of a tool used in a procedure performed by an operator of an imaging system on a human subject, and an image of anatomy of the human subject;
    acquiring images of a patient marker attached to the human subject and of the tool, wherein the images are acquired by a camera attached to a head-mounted display of the imaging system configured to be worn by the operator while the operator operates on the human subject using the tool;
    analyzing one or more images of the acquired images of the patient marker and the tool, so as to identify whether the camera is located on a first side or on a second, opposing side of a sagittal plane of the human subject, or whether the camera is located on a first side or on a second, opposing, side of an axial plane of the human subject; and
    rendering to the head-mounted display the image of the anatomy of the human subject with the graphical representation of the tool superimposed thereon from a point of view in the identified side of the human subject.

2. The method according to claim 1, wherein the analyzing of the one or more acquired images comprises identifying if the camera moves from a first side to a second, opposing, side of the sagittal or axial plane of the human subject, and if the camera moves from the first side to the opposing side of the sagittal or axial plane of the human subject, the rendering of the image of the anatomy of the human subject with the graphical representation of the tool superimposed thereon comprises mirroring the image of the anatomy of the human subject with the graphical representation of the tool superimposed thereon with respect to the sagittal or axial plane, correspondingly.

3. The method according to claim 1, wherein the image of anatomy of the human subject is a two-dimensional image.

4. The method according to claim 1, wherein the tool comprises identifying tool-reflectors attached thereto, and wherein the patient marker comprises optically reflective elements disposed on the patient marker so as to define at least one plane of asymmetry thereon, by being disposed on opposing sides of the at least one plane of asymmetry in a non-symmetrical arrangement with respect to the at least one plane of asymmetry, so that the elements on a first side of the at least one plane of asymmetry do not mirror, through the at least one plane of asymmetry, the elements on a second, opposing, side of the at least one plane of asymmetry.

5. The method according to claim 4, wherein the defined at least one plane of asymmetry of the patient marker is parallel to the sagittal or axial plane of the human subject, and wherein analyzing the acquired images comprises identifying whether the camera is located on a first side or on a second, opposing side of the defined at least one plane of asymmetry, and the rendering comprises rendering the image of the anatomy of the human subject with the graphical representation of the tool superimposed thereon from a point of view in the identified side of the defined at least one plane of asymmetry.

6. The method according to claim 4, wherein the at least one plane of asymmetry makes an angle between +20° and −20° with the sagittal or axial plane of the human subject, correspondingly.

7. The method according to claim 4, wherein the patient marker defines a further plane and wherein the optically reflective elements are disposed on opposing sides of the further plane in a non-symmetrical arrangement with respect to the further plane, further comprising analyzing the one or more images of the acquired images so as to identify the further plane and to identify a side of the further plane wherein the camera is located, and to render to the display the image of the anatomy of the human subject with the graphical representation of the tool superimposed thereon from a point of view in the identified side of the further plane.

8. The method according to claim 1, wherein the camera is located at a vertical height above the patient marker, the method further comprising:
ascertaining the vertical height in response to acquiring images of the patient marker and the tool;
calculating a pair of planes, each of the pair having a preset acute angle to one of the sagittal plane or the axial plane of the human subject and defining a first acute-angled wedge region and a second acute-angled wedge region to the one of the planes; and
when the display moves so that the point of view crosses the first acute-angled wedge region and the second acute-angled wedge region, or begins within the first acute-angled wedge region and crosses the second acute-angled wedge region, while the camera remains at the vertical height, rendering to the display the image of the anatomy of the human subject with the graphical representation of the tool superimposed thereon from a point of view in a side of the human subject opposite the identified side of the human subject.

9. The method according to claim 1, wherein the camera is located at a vertical height above the patient marker, the method further comprising:
ascertaining the vertical height in response to acquiring images of the patient marker; and
when the display moves so that the vertical height changes, rendering unchanged to the head-mounted display the image of the anatomy of the human subject with the graphical representation of the tool superimposed thereon.

10. The method according to claim 1, further comprising:
analyzing additional images of the patient marker and the tool acquired by an additional camera, so as to identify whether the additional camera is located on a first side or on a second, opposing side, of the sagittal or axial plane of the human subject, wherein the additional camera is attached to an additional head-mounted display of the imaging system configured to be worn by an additional operator of the imaging system; and
render to the additional head-mounted display the image of the anatomy of the human subject with the graphical representation of the tool superimposed thereon from an additional point of view in the side of the human subject identified as the side in which the additional camera is located.

11. The method according to claim 10, wherein when the operator is located on a first side of the sagittal or axial plane of the human subject and the additional operator is located on the second, opposing side of the sagittal or axial plane of the human subject, correspondingly, the rendering to the additional head-mounted display of the image of the anatomy of the human subject with the graphical representation of the tool superimposed thereon comprises mirroring the image of the anatomy of the human subject with the graphical representation of the tool superimposed thereon rendered to the head-mounted display with respect to the sagittal or axial plane correspondingly.

12. An imaging system, comprising:
a head-mounted display configured to be worn by an operator of the system;
a memory configured to store a graphical representation of a tool used in a procedure performed by the operator on the human subject, and an image of anatomy of the human subject;
a camera attached to the head-mounted display and configured to acquire images of a patient marker attached to the human subject and of the tool, while the operator operates on the human subject using the tool; and
at least one processor configured to:
analyze one or more images of the acquired images of the patient marker and the tool, so as to identify whether the camera is located on a first side or on a second, opposing side of a sagittal plane of the human subject, or whether the camera is located on a first side or on a second, opposing, side of an axial plane of the human subject; and
render to the head-mounted display the image of the anatomy of the human subject with the graphical representation of the tool superimposed thereon from a point of view in the identified side of the human subject.

13. The imaging system according to claim 12, wherein the analyzing of the one or more acquired images comprises identifying if the camera moves from a first side to a second, opposing, side of the sagittal or axial plane of the human subject, and if the camera moves from the first side to the opposing side of the sagittal or axial plane of the human subject, the rendering of the image of the anatomy of the human subject with the graphical representation of the tool superimposed thereon comprises mirroring the image of the anatomy of the human subject with the graphical representation of the tool superimposed thereon with respect to the sagittal or axial plane, correspondingly.

14. The imaging system according to claim 12, wherein the image of anatomy of the human subject is a two-dimensional image.

15. The imaging system according to claim 12, wherein the tool comprises identifying tool-reflectors attached thereto, and wherein the patient marker comprises optically reflective elements disposed on the patient marker so as to define at least one plane of asymmetry thereon, by being disposed on opposing sides of the at least one plane of asymmetry in a non-symmetrical arrangement with respect to the at least one plane of asymmetry, so that the elements on a first side of the at least one plane of asymmetry do not mirror, through the at least one plane of asymmetry, the elements on a second, opposing, side of the at least one plane of asymmetry.

16. The imaging system according to claim 15, wherein the defined at least one plane of asymmetry of the patient marker is parallel to the sagittal or axial plane of the human subject, and wherein the analyzing of the acquired images comprises identifying whether the camera is located on a first side or on a second, opposing side of the defined at least one plane of asymmetry, and the rendering comprises rendering the image of the anatomy of the human subject with the graphical representation of the tool superimposed thereon from a point of view in the identified side of the defined at least one plane of asymmetry.

17. The imaging system according to claim 12, wherein the camera is located at a vertical height above the patient marker, and the processor is further configured:
to ascertain the vertical height in response to the acquired images of the patient marker and the tool;
to calculate a pair of planes, each of the pair having a preset acute angle to one of the sagittal plane or the axial plane of the human subject and defining a first acute-angled wedge region and a second acute-angled wedge region to the one of the planes; and
when the display moves so that the point of view crosses the first acute-angled wedge region and the second acute-angled wedge region, or begins within the first acute-angled wedge region and crosses the second acute-angled wedge region, while the camera remains at the vertical height, to render to the display the image of the anatomy of the human subject with the graphical representation of the tool superimposed thereon from the point of view in a side of the human subject opposite the identified side of the human subject.

18. The imaging system according to claim 12, wherein the camera is located at a vertical height above the patient marker, and the processor is configured:
to ascertain the vertical height in response to the acquired images of the patient marker; and
when the head-mounted display moves so that the vertical height changes, to render unchanged to the head-mounted display the image of the anatomy of the human subject with the graphical representation of the tool superimposed thereon.

19. The imaging system according to claim 12, further comprising:
an additional head-mounted display configured to be worn by an additional operator of the imaging system;
an additional camera attached to the additional head-mounted display and configured to acquire additional images of the patient marker and the tool,
wherein the processor is further configured to:
analyze the additional images of the patient marker and the tool, so as to identify whether the additional camera is located on a first side or on a second, opposing side, of the sagittal or axial plane of the human subject; and
render to the additional head-mounted display the image of the anatomy of the human subject with the graphical representation of the tool superimposed thereon from an additional point of view in the side of the human subject identified as the side in which the additional camera is located.

20. The imaging system according to claim 19, wherein when the operator is located on a first side of the sagittal or axial plane of the human subject and the additional operator is located on the second, opposing side of the sagittal or axial plane of the human subject, correspondingly, the rendering to the additional head-mounted display of the image of the anatomy of the human subject with the graphical representation of the tool superimposed thereon comprises mirroring the image of the anatomy of the human subject with the graphical representation of the tool superimposed thereon rendered to the head-mounted display with respect to the sagittal or axial plane, correspondingly.

\* \* \* \* \*